(12) United States Patent
Charych et al.

(10) Patent No.: US 7,148,058 B2
(45) Date of Patent: Dec. 12, 2006

(54) PROTEIN MICROARRAYS ON MIRRORED SURFACES FOR PERFORMING PROTEOMIC ANALYSES

(75) Inventors: Deborah Charych, Albany, CA (US); Ronald N. Zuckermann, El Cerrito, CA (US)

(73) Assignee: Chiron Corporation, Emeryville, CA (US)

( * ) Notice: Subject to any disclaimer, the term of this patent is extended or adjusted under 35 U.S.C. 154(b) by 99 days.

(21) Appl. No.: 10/190,433

(22) Filed: Jul. 3, 2002

(65) Prior Publication Data

US 2003/0013130 A1    Jan. 16, 2003

Related U.S. Application Data

(63) Continuation-in-part of application No. 09/874,091, filed on Jun. 4, 2001.

(60) Provisional application No. 60/209,711, filed on Jun. 5, 2000.

(51) Int. Cl.
| C12M 1/34 | (2006.01) |
| C40B 40/00 | (2006.01) |
| C40B 40/10 | (2006.01) |
| G01N 33/53 | (2006.01) |
| C40B 50/18 | (2006.01) |

(52) U.S. Cl. ................ 435/287.8; 435/7.1; 435/287.1; 435/287.2; 435/288.7; 435/DIG. 34; 435/DIG. 35; 435/DIG. 36; 435/DIG. 40; 435/DIG. 43; 436/518; 436/524; 436/525; 436/527; 436/535

(58) Field of Classification Search .............. 435/4, 435/7.1, 287.1, 287.2, 810, 283.1, 287.8, 435/288.7, DIG. 1, DIG. 34, DIG. 35, DIG. 36, 435/DIG. 40; 436/518, 524, 527, 535
See application file for complete search history.

(56) References Cited

U.S. PATENT DOCUMENTS

| 4,963,263 A | | 10/1990 | Kauvar |
| 5,091,318 A | * | 2/1992 | Anawis et al. .............. 436/513 |
| 5,133,866 A | | 7/1992 | Kauvar |
| 5,340,474 A | | 8/1994 | Kauvar |
| 5,409,611 A | | 4/1995 | Kauvar |
| 5,478,527 A | * | 12/1995 | Gustafson et al. ........ 422/82.11 |
| 5,482,867 A | | 1/1996 | Barrett et al. |
| 5,556,942 A | | 9/1996 | Kauvar et al. |
| 5,567,317 A | | 10/1996 | Kauvar |
| 5,599,903 A | | 2/1997 | Kauvar et al. |
| 5,624,711 A | | 4/1997 | Sundberg et al. |
| 5,763,570 A | | 6/1998 | Kauvar et al. |
| 5,767,086 A | | 6/1998 | Kauvar et al. |
| 5,786,336 A | | 7/1998 | Kauvar et al. |
| 5,831,005 A | | 11/1998 | Zuckerman et al. |
| 5,831,070 A | | 11/1998 | Pease et al. |
| 5,955,432 A | | 9/1999 | Kauvar et al. |
| 5,965,695 A | | 10/1999 | Simon et al. |
| 6,013,462 A | | 1/2000 | Kauvar et al. |
| 6,221,994 B1 | * | 4/2001 | Galbiati et al. .............. 528/26 |
| 6,329,209 B1 | * | 12/2001 | Wagner et al. ............. 436/518 |
| 6,406,921 B1 | | 6/2002 | Wagner et al. |

FOREIGN PATENT DOCUMENTS

| DE | 197 41 716 A1 | 3/1999 |
| WO | WO 89/09088 | 10/1989 |
| WO | WO 91/06356 | 5/1991 |
| WO | WO 92/10757 | 6/1992 |
| WO | WO 98/31839 | 7/1998 |
| WO | WO 98/42730 | 10/1998 |
| WO | WO 98/53304 | 11/1998 |
| WO | WO 98/59360 | 12/1998 |
| WO | WO 99/48897 | 9/1999 |
| WO | WO 00/11208 | 3/2000 |
| WO | WO 01/01142 | 1/2001 |
| WO | WO 01/94946 A | 12/2001 |

OTHER PUBLICATIONS

Weetall, H. H., "Preparation of immobilized Proteins Covalently Coupled Through Silane Coupling Agents to Inorganic Supports", 1993, Applied Biochemistry and Biotechnology, 41, 157-188. (NOTE: In PTO-1449 dated Jan. 27, 2003.).*

(Continued)

*Primary Examiner*—Peter Pakas, Jr.
*Assistant Examiner*—My-Chau T Tran
(74) *Attorney, Agent, or Firm*—James E. Austin; Young J. Suh; Alisa A. Harbin

(57) ABSTRACT

Provided are protein microarrays, their manufacture, use, and application. Protein microarrays in accordance with the present invention are useful in a variety preoteomic analyses. Various protein arrays in accordance with the present invention may immobilize large arrays of proteins that may be useful for studying protein-protein interactions to improve understanding of disease processes, facilitating drug discovery, or for identifying potential antigens for vaccine development. The protein array elements of the invention are native or modified proteins (e.g., antibodies or fusion proteins). The protein array elements may be attached directly to a organic functionalized mirrored substrate by a binding reaction between functional groups on the substrate (e.g., amine) and protein (e.g., activated carboxylic acid). Techniques for chemical blocking of the arrays are also provided. The invention contemplates spotting of array elements onto solid planar substrates, labeling of complex protein mixtures, and the analysis of protein binding to the array. The invention also enables the enrichment or purification, and subsequent sequencing or structural analysis of proteins that are identified as differential by the array screen. Kits including protein-binding microarrays for proteomic analysis in accordance with the present invention are also provided.

34 Claims, 8 Drawing Sheets

OTHER PUBLICATIONS

Hruby, et al., "Synthesis of oligopeptide and peptidomimetic libraries", Department of Chemistry, University of Arizona, Current Opinion in Chemical Biology, 1997, 1:114-119.

Ripka, et al., "Peptidomimetic design", Department of Chemistry and School of Pharmacy, University of Wisconsin-Madison, Current Opinion in Chemical Biology, 1998, 2:441-452.

Al-Obeidi, et al., "Peptide and Peptidomimetic Libraries", Molecular Diversity and Drug Design, Molecular Biotechnology, 1998, vol. 9, pp. 205-223.

Berry, et al., "Use of Antibody Fragments in Immunoaffinity Chromatography" Comparison of FV Fragments, VH Fragments and Paralog Peptides, Journal of Chromatography, Chrom. 23 869, 1992, pp. 239-245.

Chapman, et al., "Surveying for Surfaces that Resist the Absorption of Proteins", Department of Chemistry and Chemical Biology, Harvard University, Received Mar. 3, 2000, pp. 8303-8304.

Houry, et al., "Identification of in Vivo Substrates of the Chaperonin GroEL", Department of Cellular Biochemistry, Nature vol. 402, Nov. 11, 1999, pp. 147-154.

Kauvar, et al., "Paralog Chromatography", Research Report, Terrapin Technologies, Inc. and Rice University, vol. 8, No. 2, 1990, pp. 204-206.

Martzen, et al., "A Biochemical Genomics Approach for Identifying Genes by the Activity of Their Products", Reports, vol. 286, Nov. 5, 1999, pp. 1153-1155.

Rajur, et al., "Combinatorial Synthesis of N-Substituted α-Amino Acids on Sepharose" Lecture Programme and Abstract Book, Solid Phase Synthesis & Combinatorial Chemical Libraries, The European Peptide Society & BS/RSC Protein and Peptide Science Group, UK, Dates: Aug. 31-Sep. 4, 1999, Abstract.

"The Promise of Proteomics", Nature, Macmillian Magazines Ltd, Dec. 16, 1999, vol. 402, Issue No. 402, p. 703.

Weetall, Preparation of immobilized proteins covalently coupled through silane coupling agents to inorganic support, 1993, vol. 41, 157-188.

"Redrawn Capillary Imaging Reservoir", Nov. 10, 1999, p. 1, abstract only.

"Array for Generating Combinatorial Libraries", May 17, 2001, p. 1, abstract only.

Falsey, et al., "Peptide and Small Molecule Microarray for High Throughput Cell Adhesion and Functional Arrays", UC Davis Cancer Center, Bioconjugate Chem., Received Nov. 21, 2000, vol. 12, No. 3, pp. 346-353.

MacBeath, et al., "Printing Proteins as Microarrays for High-Throughput Funcation Determination", Sep. 8, 2000, vol. 289, pp. 1760-1763.

Hergenrother, et al., "Small-Molecule Microarrays: Covalent Attachment and Screening of Alcohol-Containing Small Molecules on Glass Slides", Department of Chemistry and Chemical Biology, Received on Apr. 22, 2000, vol. 122, No. 32, pp. 7849-7850.

"Device for Carrying Out an Almost Simultaneous Synthesis of a Plurality of Samples", Dec. 29, 1999, p. 1, abstract only.

"Surface Plasmon Resonance Sensor for the Simultaneous Measurement of a Plurality of Samples in Fluid Form", Nov. 25, 1999, p. 1, abstract only.

"The Array for the High-Throughput Synthesis, Screening and Characterization of Combinatorial Libraries, and Methods for Making the Array", May 17, 2001, p. 1, abstract only.

Zhu et al., "Global Analysis of Protein Activities Using Proteome Chips", Science, vol. 293, Sep. 14, 2001, pp. 2101-2105.

Fang, et al., "Membrane Protein Microarrays", JACS Communications, Biochemical Technologies, Science and Technology Division, vol. 124, No. 11, Received Oct. 22, 2001, Published on Web Feb. 26, 2002, pp. 2394-2395.

Mecklenburg, Michael, "XNA on Gold™: a versatile microarray platform", pp. 61-62, poster abstract.

Haab, et al, "Protein microarrays for highly parallel detection and quantitation of specific proteins and antibodies in complex solutions", Genome Biology, vol. 2, No. 2, Received: Nov. 9, 2000, Revised: Dec. 5, 2000, Accepted: Dec. 13, 2000, pp. 0004.1-0004.13.

MacBeth et al., "Printing Small Molecules as Microarrays and Detecting Protein—Ligand Interactions en Masse" J. Am. Chem. Soc. 121:7967-7968, 1999.

Pirrung et al., "A General Method for the Spatailly Defied Imobilization of Biomolecules on Glass Surface Using 'Caged' Biotin" Bioconjugate Chem. 7:317-321, 1996.

European Search Report dated Mar. 4, 2006 from related European Application No. 03763248.6—PCT/US-321127.

\* cited by examiner

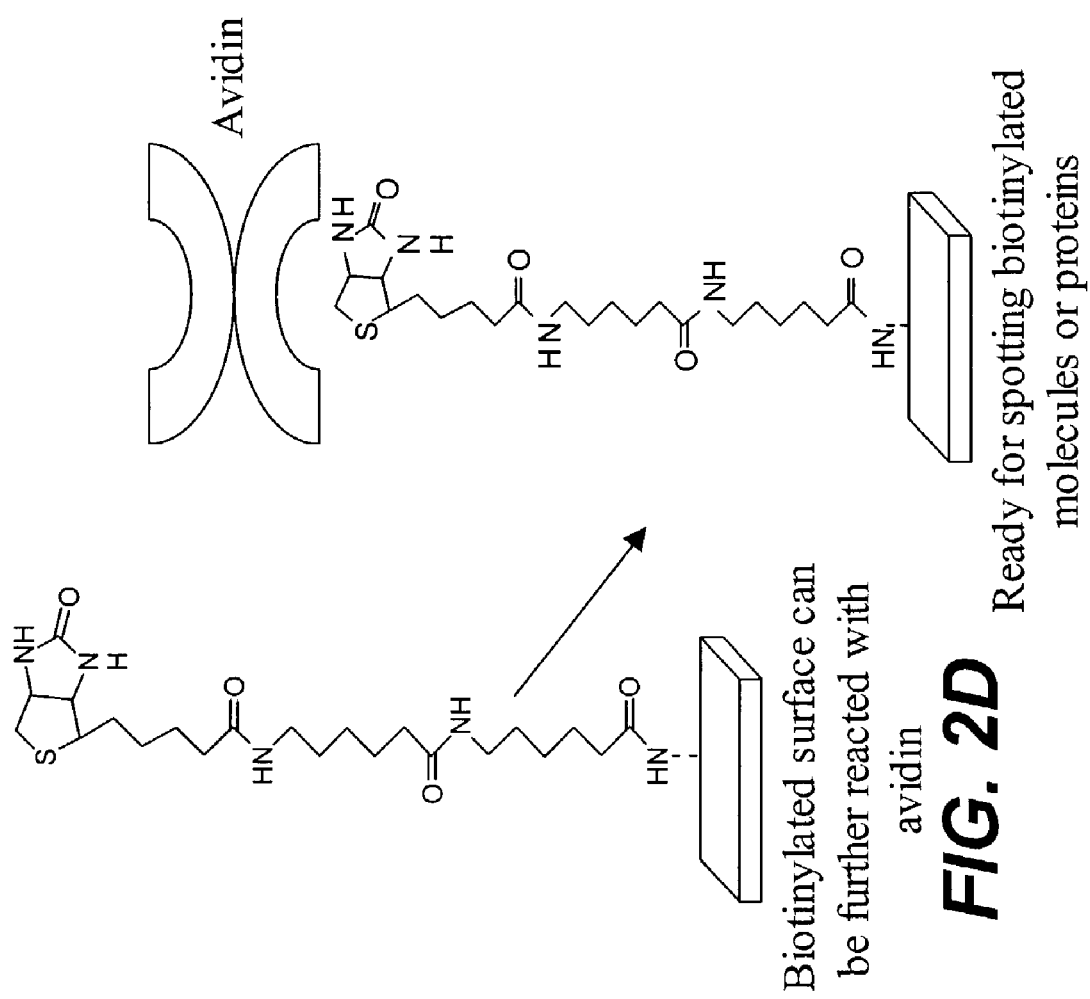
FIG. 2D Biotinylated surface can be further reacted with avidin
FIG. 2E Ready for spotting biotinylated molecules or proteins

PROTEIN MICROARRAYS ON MIRRORED SURFACES FOR PERFORMING PROTEOMIC ANALYSES

CROSS-REFERENCE TO RELATED APPLICATIONS

This application is a continuation-in-part of U.S. patent application Ser. No. 09/874,091 titled MICROARRAYS FOR PERFORMING PROTEOMIC ANALYSES, filed Jun. 4, 2001; which claims priority from U.S. Provisional Application No. 60/209,711, entitled MICROARRAYS FOR PERFORMING PROTEOMIC ANALYSES, filed Jun. 5, 2000; the disclosure of each of which is incorporated by reference herein in its entirety for all purposes.

BACKGROUND OF THE INVENTION

1. Field of the Invention

The present invention relates to cell product analysis and materials. More specifically, the invention is directed to protein-displaying microarrays, methods of making them and methods of using them to conduct highly sensitive proteomic analyses.

2. Description of Related Art

In recent years, microarray technology has developed from a specialized sub-field into an important tool for basic and applied studies in molecular biology, microbiology, pharmaceutics, agriculture, and many other biotechnologies. DNA microarray technology attempts to link the genome of an organism or cell to an expressed phenotype or protein function.

The overwhelming publication and patent literature on microarray technology describes arrays of DNA (or other forms of nucleic acid, such as cDNA or RNA), displayed on a solid surface such as a glass slide (often referred to as a "chip"). The arrayed DNA is typically in the form of short oligonucleotides (e.g., about 8 to 25 bases) or longer clones or PCR products (about 500 to 2000 bases). The former are typically synthesized on the solid support, whereas the latter are robotically "spotted" onto a solid support into an array format.

While there are reports of peptide and protein arrays on solid surfaces, these have received considerably less attention in comparison to DNA arrays. This is likely due to the inherent instability of these materials at interfaces, and in the presence of complex biological matrices. For example, it is well known, that many proteins denature upon contact with solid surfaces. In addition, the mode in which the protein is displayed may markedly affect how it interacts with a binding partner. For example, the binding site of the protein may be oriented in the direction opposite to the interface, preventing specific binding interactions. Therefore, the orientation of the protein at the array surface may play a significant role in the applicability of protein array devices.

Currently, the most common way of analyzing the proteome of biological samples employs two-dimensional ("2-D") gel electrophoresis. This method is problematic because the results are very sensitive to the experimental protocol (for example, development time of the gel as well as other parameters). Therefore, it is very difficult to obtain reproducible data from 2-D gels. Also, the sensitivity of the silver stain used in these gels is limited, and is less than that of the fluorescent labels used in microarray technologies.

Thus, there is an overwhelming need to develop effective microarray technology that is useful in a protein context. In many cases, functional pathways cannot be directly linked to a particular gene. Proteins often undergo a variety of post-translational modifications, interactions, or degradations that ultimately determine function. Even the seemingly simple evaluation of a protein's abundance cannot be directly correlated with the level of corresponding mRNA. The only solution is to evaluate the state of the cell, tissue or organism at the protein level. Therefore, a high throughput format that allows rapid display of protein differentials in complex mixtures such as cells, tissues, serum, etc., would provide a powerful counterpart and complement to DNA microarray technology.

SUMMARY OF THE INVENTION

To achieve the foregoing, the present invention provides protein-displaying microarrays (also referred to herein as "protein microarrays"), their manufacture, use, and application. In particular, the invention provides arrays that produce enhanced signals due to the use of a mirrored array substrate surface in an assay in which fluorescently labeled binding partners interact with an array element bound to the substrate surface (e.g., Cy3 or Cy5 other fluorescent probes), referred to herein as "fluorescence array scanning" or "scanning." A variety of commercially array scanners are available primarily for use in cDNA array scanning. Such sensitive protein microarrays in accordance with the present invention are useful in a variety preoteomic analyses. Various protein arrays in accordance with the present invention may immobilize large arrays of proteins that may be useful for studying protein-protein interactions to improve understanding of disease processes, facilitating drug discovery, or for identifying potential antigens for vaccine development.

The protein array elements displayed by microarrays in accordance with the present invention are native or modified proteins (e.g., antibodies). The protein array elements may be attached directly or indirectly to an organic functionalized substrate by a binding reaction between functional groups on the substrate (e.g., amine or maleimide) and protein (e.g., activated carboxylic acid or thiol), or may use tags on the protein (such as glutathione-S-transferase) that interact non-covalently with cognate ligands or proteins displayed on the surface (such as glutathione). The invention contemplates spotting of array elements onto mirrored solid planar substrates, labeling of complex protein mixtures, detection of protein biomarkers, and the analysis of differential protein binding to the array. The invention also enables the enrichment or purification, and subsequent sequencing or structural analysis of proteins that are identified as differential by the array screen. Kits including protein-binding microarrays for proteomic analysis in accordance with the present invention are also provided.

In one aspect, the invention pertains to an array of proteins displayed on the surface of a solid support. The array includes a solid substrate having a substantially planar dielectric coating layer with thickness optimized to amplify fluorescence from particular wavelengths, on a reflective ("mirrored") metal surface The dielectric is preferably an oxide, for example silicon dioxide ($SiO_2$). The dielectric coating layer is organically functionalized to allow a plurality of different protein array elements to bind to the substrate surface. Each of the array elements is a protein of interest, in native or modified form stably attached to the substrate surface. The binding of the array element may optionally be via a stably bound adapter, stably bound to the substrate surface.

In specific embodiments of the invention, the array further includes a chemical block: a further derivatization of the substrate surface with one or more species that specifically bind to complementary molecules displayed on the substrate surface to inhibit non-specific protein adsorption. The chemical block is generally a synthetic homopolymer or homo-oligomer. Examples include polyethyleneglycol (PEG) and PEG analogs based on oligomeric N-substituted glycines or peptoids (e.g., other inert hydrophilic polymers) with termini that bind to the substrate. Treatment of the substrate surface with such a chemical block following spotting of the array elements has been shown to decrease non-specific protein binding to the array (and to therefore increase array sensitivity and resolution. Such treatment allows detection of labeled proteins in complex protein mixtures such as complex biological mixtures such as cell lysates, serum, whole blood, urine, and other body fluids which would otherwise obfuscate the fluorescent signal due to extensive non-specific binding of the labeled mixture. In such extreme cases, conventional blocking agents such as casein, bovine serum albumin and the like (protein blocks) may not provide sufficient blocking of non-specific protein binding.

In another aspect, the invention pertains to a method of making an array comprising a plurality of different proteins stably associated with the surface of a mirrored solid support. The method involves preparing for bonding a solid substrate having a substantially planar surface, and contacting a plurality of different protein array elements with the substrate under conditions sufficient for the protein array elements to become bound to the substrate surface. The array includes a solid substrate having a substantially planar dielectric coated and functionalized reflective metal surface, and a plurality of different protein array elements bound to the substrate surface. The thickness of the dielectric layer is adjusted to allow maximal detection of specific excitation and fluorescent wavelengths during the actual analysis of protein binding. Each of the array elements includes a protein and, optionally, a stably bound adapter, stably bound to the substrate surface. The array may further include a further derivatization of the substrate surface with one or more species that inhibit protein adsorption (e.g., PEG or analogs (other inert polymers with termini that bind to substrate surface) following spotting of the array elements. As noted above, such treatment allows detection of labeled proteins in complex biological mixtures such as cell lysates, serum, whole blood, urine, and other body fluids which would otherwise obfuscate the fluorescent signal due to extensive non-specific binding of the labeled mixture. In such extreme cases, conventional blocking agents such as casein, bovine serum albumin and the like (protein blocks) may not provide sufficient blocking of non-specific protein binding.

A further aspect of the present invention pertains to a method of performing a differential binding assay. The method involves labeling proteins in a protein-containing biological sample solution, contacting an aliquot of the labeled protein-containing biological sample solution with an array as described herein, and analyzing the array to determine differential binding of proteins in the sample to protein-binding agents of the array. In this mode, the inhibition of non-specific binding of other proteins in the complex mixture are of particular importance.

Another aspect of the present invention pertains to a kit for use in performing a differential binding assay as described herein. The kit includes an array having a solid substrate having a substantially planar surface with a plurality of different protein agents bound to the substrate.

The invention also pertains to the detection of specific proteins that may act as biomarkers in a mixture. For example, one might follow the fate of a set of proteins as they increase or decrease in concentration in response to a drug, for example, or other treatment.

The arrays of the present invention may be usefully applied to the detection of antibodies in serum against potential protein antigens spotted on the array. These studies may help to determine immune response in these patients in order to identify immune-stimulating antigens. By discovering the appropriate antigens, new vaccines may be developed.

These and other features and advantages of the present invention will be presented in more detail in the following specification of the invention and the accompanying figures which illustrate by way of example the principles of the invention.

BRIEF DESCRIPTION OF THE DRAWINGS

FIGS. 2A–2E schematically depict alternative modes of binding a protein array element to a solid support in accordance with specific embodiments of the present invention.

DESCRIPTION OF SPECIFIC EMBODIMENTS OF THE INVENTION

Figure 1A:
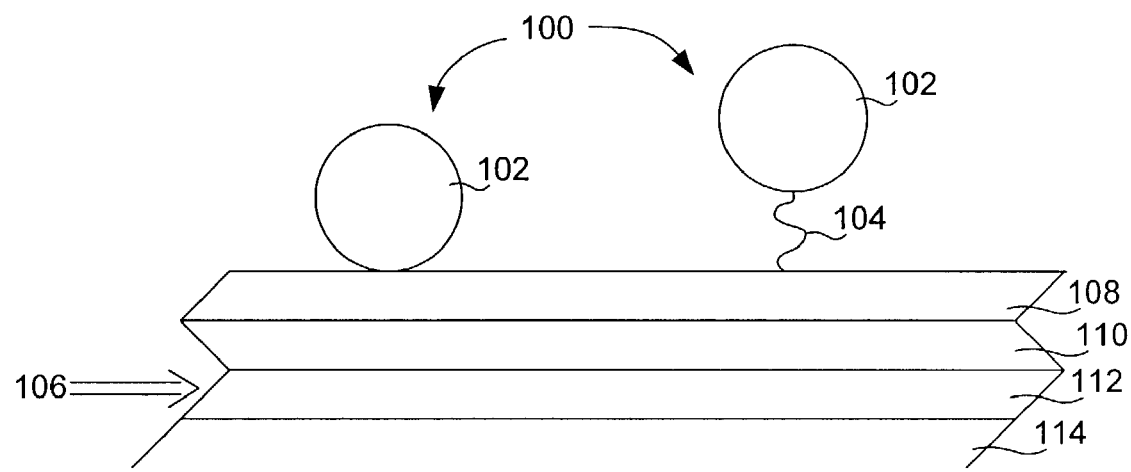
FIGS. 1A and 1B schematically depict the structure of a protein-binding agent array element and array portion, respectively, in accordance with one embodiment of the present invention.

The materials and associated techniques and apparatuses of the present invention will now be described with reference to several embodiments. Important properties and characteristics of the described embodiments are illustrated in the structures in the text and in the accompanying drawings. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

When used in combination with "comprising," "a method comprising," "an apparatus comprising" or similar language in this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Introduction

The present invention provides protein-displaying microarrays (also referred to herein as "protein microarrays"), their manufacture, use, and application. The different protein array elements of the invention are stably attached to a mirrored solid support directly or indirectly. Protein microarrays in accordance with the present invention are useful in a variety preoteomic analyses. Various protein arrays in accordance with the present invention may immobilize large arrays of proteins (e.g., antibodies) that may be useful for studying protein-protein interactions to improve understanding of disease processes, to deduce the mechanisms of drug action by monitoring levels of specific proteins in a mix, facilitating drug discovery, or for identifying potential antigens for vaccine development. The invention also enables the enrichment or purification, and subsequent sequencing or structural analysis, of proteins that are identified as differential by the array screen. Kits including proteomic microarrays in accordance with the present invention are also provided.

In particular, the invention provides arrays that produce enhanced signals due to the use of a mirrored array substrate surface in an assay in which fluorescently labeled binding partners interact with an array element bound to the substrate surface (e.g., Cy3 or Cy5 other fluorescent probes), referred to herein as "fluorescence array scanning" or "scanning." A variety of commercially array scanners are available primarily for use in cDNA array scanning. Such sensitive protein microarrays in accordance with the present invention are useful in a variety of preoteomic analyses. Various protein arrays in accordance with the present invention may immobilize large arrays of proteins that may be useful for studying protein-protein interactions to improve understanding of disease processes, facilitating drug discovery by discovery of novel drug targets, for identifying biomarkers associated with a disease state, for monitoring protein levels in response to a drug or other stimulus, or for identifying potential antigens for vaccine development.

The protein array elements displayed by microarrays in accordance with the present invention are native or modified proteins (e.g., antibodies or protein fusions). The protein array elements may be attached directly or indirectly to an organic functionalized substrate by a binding reaction between functional groups on the substrate (e.g., amine or maleimide) and protein (e.g., activated carboxylic acid or thiol), or may use tags on the protein (such as glutathione-S-transferase) that interact non-covalently with cognate ligands or proteins displayed on the surface (such as glutathione). The invention contemplates spotting of array elements onto mirrored solid planar substrates, labeling of complex protein mixtures, detection of protein biomarkers, and the analysis of differential protein binding to the array. The invention also enables the enrichment or purification, and subsequent sequencing or structural analysis of proteins that are identified as differential by the array screen. Kits including protein-binding microarrays for proteomic analysis in accordance with the present invention are also provided.

In one aspect, the invention pertains to an array of proteins displayed on the surface of a solid support. The array includes a solid substrate having a substantially planar dielectric coating layer with thickness optimized to amplify fluorescence from particular wavelengths, on a reflective ("mirrored") metal surface The dielectric is preferably an oxide, for example silicon dioxide ($SiO_2$). The dielectric coating layer is organically functionalized to allow a plurality of different protein array elements to bind to the substrate surface. Each of the array elements is a protein of interest, in native or modified form stably attached to the substrate surface. The binding of the array element may optionally be via a stably bound adapter, stably bound to the substrate surface. In various specific embodiments, arrays in accordance with the present invention may take the form of a protein bound to directly to the functionalized substrate surface; a protein bound to the substrate surface via a bifunctional adapter; a protein-avidin conjugate bound to the substrate surface via a biotin functionality of the substrate surface; a biotinylated protein bound to an avidin functionality of the substrate surface; a protein bound to a complementary protein functionality of the substrate surface (e.g., the array element may be an antibody and the substrate surface may be functionalized with an adapter terminating in Protein A or Protein G); each array element may be a fusion protein bound to a complementary protein functionality of the substrate surface, e.g., the array element may be an GST-fusion protein and the substrate surface may be functionalized with an adapter terminating in glutathione, or a fusion of EYMPME (glu) peptide that would attach to Anti-glu antibody on the substrate, or a fusion with His-6 attached to a metal (e.g., nickel) chelate on the substrate, or a fusion with DYKDDDDK peptide ("FLAG") attached to anti-FLAG on the surface, or a fusion with maltose binding protein attached to maltose or maltodextrins on the surface; or other known protein fusions that would typically be made when expressing recombinant proteins.

In specific embodiments of the invention, the array further includes a chemical block: a further derivatization of the substrate surface with one or more species that specifically bind to complementary molecules displayed on the substrate surface to inhibit non-specific protein adsorption. Chemical blocks (chemical blocking agents) in accordance with the present invention are polymeric or oligomeric non-proteins, generally synthetic homopolymers, for example, polyethyleneglycol (PEG), PEG analogs, or other inert hydrophilic polymers (e.g., hydrophilic N-substituted glycines or peptoids) with one or more termini that bind to the substrate. For example, the chemical blocking agent for a maleimide functionalized substrate surface may be a thiol-modified polyethylene glycol (PEG). One specific example is a dithiol-modified PEG (SH-PEG-SH), for example having a molecular weight of about 3400–5000 (for example, commercially available from Shearwater Polymers). Oligomeric blocks, such as hydrophilic N-substituted glycines or peptoids, provide chemical blocking polymers or oligomers of very well-defined molecular weight and purity. Treatment of the substrate surface with such a chemical block following spotting of the array elements has been shown to decrease non-specific protein binding to the array (and to therefore increase array sensitivity and resolution. Such treatment allows detection of labeled proteins in complex biological mixtures such as cell lysates, serum, whole blood, urine, and other body fluids which would otherwise obfuscate the fluorescent signal due to extensive non-specific binding of the labeled mixture. In such extreme cases, conventional blocking agents such as casein, bovine serum albumin and the like (referred to herein as protein blocks to distinguish them from the chemical blocks used in accordance with the present invention) may not provide sufficient blocking of non-specific protein binding.

In another aspect, the invention pertains to a method of making an array comprising a plurality of different proteins stably associated with the surface of a mirrored solid support. The method involves preparing for bonding a solid substrate having a substantially planar surface, and contacting a plurality of different protein array elements with the substrate under conditions sufficient for the protein array elements to become bound to the substrate surface. The array includes a solid substrate having a substantially planar dielectric coated and functionalized reflective metal surface, and a plurality of different protein array elements bound to the substrate surface. The thickness of the dielectric layer is adjusted to allow maximal detection of specific excitation and fluorescent wavelengths during the actual analysis of protein binding. Each of the array elements includes a protein and, optionally, a stably bound adapter, stably bound to the substrate surface. The array may further include a further derivatization of the substrate surface with one or more species that inhibit protein adsorption (e.g., PEG or analogs (other inert polymers with termini that bind to substrate surface) following spotting of the array elements. As noted above, such treatment allows detection of labeled proteins in complex biological mixtures such as cell lysates, serum, whole blood, urine, and other body fluids which would otherwise obfuscate the fluorescent signal due to extensive non-specific binding of the labeled mixture. In such extreme cases, conventional blocking agents such as casein, bovine serum albumin and the like (protein blocks) may not provide sufficient blocking of non-specific protein binding.

1. Protein Microarrays

Protein microarrays in accordance with the present invention are composed of a number of different displayed protein array elements including, for example, antibodies or fusion proteins and other synthetic proteins, attached to a mirrored surface of a solid support. The different array elements each may be directly attached to the substrate surface, or may be indirectly attached to the substrate surface via one or more chemical species, referred to herein as "adapters." As used in the present application, the terms "attached to" or "bound to" or "associated with" refer to a stable association between molecular species under normal operating conditions during the processing to which the microarray is subjected. Thus, in accordance with the present invention, the concentration and density of a suitable protein array element on a suitable substrate surface is maintained during the processing to which the microarray is subjected under its normal operating conditions, for example, as described herein. The number of different protein array elements present on the surface of a microarray in accordance with the present invention is at least 2, may be 10 or more, or 100 or more, and may be much higher, generally being at least about 1,000, and may be from about 5,000 to about 50,000, for example, between about 5,000 and about 10,000, as described further below.

Figure 1B:
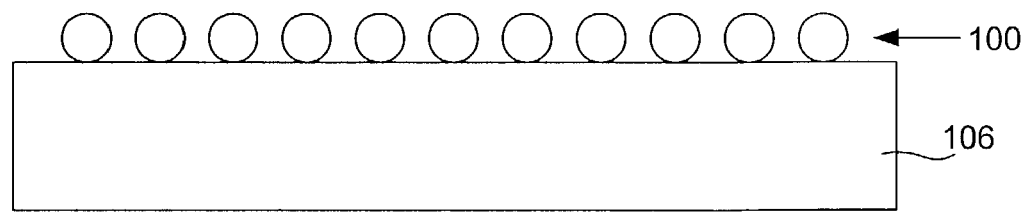

FIGS. 1A and 1B provide representations of types of array elements and one type of array, respectively, in accordance with the present invention. As shown in FIG. 1A, a protein array element 100 is a protein 102 attached to the surface of the solid substrate 106. The protein may be in its native state, or it may be modified in some way that ideally preserves its native binding properties. Examples of such modifications include chemical reduction or activation of certain functional groups (e.g., thiol or carboxylic acid groups, respectively) to facilitate binding to the substrate, or the formation of fusion proteins (e.g., GST-protein fusions). The protein 102 of the array element may be attached to the substrate directly or via a suitable molecular entity 104, referred to herein as an "adapter," suitable to facilitate the attachment of the protein array element to the surface of the solid substrate 106.

The substrate is generally composed of a plurality of layers including a solid support layer 114 having a reflective metal ("mirrored") surface layer 112, a dielectric (e.g., oxide) layer 110 and an organic surface modification layer 108 suitable to facilitate the attachment of an array element 102 to the substrate 106, optionally via an adapter 104. FIG. 1B shows simplified view of a protein array including a plurality of different array elements 100, such as illustrated in FIG. 1A, attached to a planar substrate 106. Other features of arrays in accordance with the present invention, such as inter-element molecular species applied to the substrate to reduce non-specific binding of proteins of the array are not visible in this high level depiction. Each of these array element types and components, and the formation and composition of arrays in accordance with the present invention is described in greater detail separately below.

A. Array Substrate

The substrate (FIGS. 1A and 1B, element 106) employed in arrays in accordance with the present invention may vary greatly depending on the intended use of the product to be produced. The solid support 114 may be any suitable material for supporting the reflective metal layer 112 that provides the mirrored surface and is also compatible with any analytical methods with which the array is to be used, and comprises an impermeable, rigid material. Compatibility can be determined using methods and materials known to those having skill in the surface or materials chemistry arts. In one preferred embodiment, the solid support is a glass microscope slide. Suitable materials also include glasses, such as those formed from quartz, or silicon; and metals (including alloys), e.g., gold, platinum, silver, copper, aluminum, titanium, chromium, rhodium and the like. Other suitable solid support materials include plastics, such as polymers, e.g. polyvinylchloride, polyethylene, polystyrenes, polyacrylates, polycarbonate and copolymers thereof, e.g., vinyl chloride/propylene polymer, vinyl chloride/vinyl acetate polymer, styrenic copolymers, and the like.

As noted above, a suitable substrate 106 for use in arrays in accordance with the present invention will have a dielectric coated mirrored surface. The substrate 106 will generally be a composite of a plurality of different layers of material, where the composition includes a base rigid, substantially planar solid support material, e.g., as represented by element 114 in FIG. 1A, and a plurality of layers on the solid support, as represented by elements 108, 110 and 112 in FIG. 1A. The solid support 114 has (in the case of a reflective metal) or is coated with a reflective metal layer 112. By reflective metal it is meant a metal that reflects at least 90% incident light in the wavelength region of interest, generally visible (400–800 nm), and possibly including longer wavelengths in the near infrared, such as 800–1100 nm, with very little (at or near 0%) light refracted into the medium. Suitable examples include aluminum, chromium, copper, gold, silver, platinum, titanium, rhodium, etc.

The reflective metal is overcoated with a dielectric 110, e.g., silicon oxide or silicon dioxide (silica) or alumina or fluoride such as MgF2 or titanium dioxide. Silicon dioxide is preferred in many embodiment. The thickness of this layer can be adjusted to optimize the signal from the fluorescing species, as described in further detail in International Patent Application No. WO 98/53304, incorporated by reference herein for all purposes. The dielectric layer (e.g., silicon dioxide) is functionalized with a bifunctional organic surface layer 108, e.g., an amino-modified silane, suitable to facilitate the attachment of an array element 100 to the substrate 106. Suitable aluminum/oxide/amino-propyl silane (APS) coated glass slides are commercially available from Amersham-Pharmacia, Amersham, England. The substrate may be in the dimensions of a standard 3"×1" microscope slide or in the shape of a 3" or 5" diameter circular wafer, for example. Other configurations will be apparent to those having skill in the surface or materials chemistry arts.

In the planar, rectangular embodiments of the above-described slides, the length of the support will generally be at least about 1 cm and may be as great as about 40 cm or more, but will usually not exceed about 30 cm and may often not exceed about 20 cm. The width of support will generally be at least about 1 cm and may be as great as about 40 cm, but will usually not exceed about 30 cm and will often not exceed about 20 cm. The height of the support will generally range from about 0.01 mm to about 10 mm, depending at least in part on the material from which the rigid substrate is fabricated and the thickness of the material required to provide the requisite rigidity. Of particular interest in many embodiments are supports having the dimensions of a standard microscope slide. One typical substrate size is about 2.54 cm×7.62 cm and about 1–2 mm thick. However, any suitable dimensions can be employed.

As noted above, in accordance with the present invention, the surface of the base solid support material has or is coated with a layer of a reflective metal, such as aluminum. In some embodiments, the solid support may be composed entirely of a metal material with a reflective surface. More commonly, the solid support will be composed of a material other than metal, e.g., a glass, and will have a surface coated with a reflective metal layer. The thickness of the metal layer will generally range from about 300 Å to about 10,000 Å, more particularly from about 750 Å to about 2,000 Å, and still more particularly from about 1,000 Å to about 1,500 Å. One specific thickness suitable for the present invention is 1000 Å. The metal layer may be deposited on the substrate surface using any suitable protocol, including e-beam deposition, vapor deposition, sputtering, electroplating and the like, as are known to those of skill in the art. An adhesion metal layer may be present between the metal layer and the substrate, where adhesion metals of interest include titanium, chromium, and the like—especially if non-adherent metals such as gold are to be deposited. When present, the adhesion metal layer will typically range in thickness between about 5 Å and about 100 Å, usually between about 25 Å and about 75 Å and in many embodiments will be about 50 Å. In some embodiments, the above-described adhesion layer can be a molecular adhesion layer. Examples of materials suitable for forming molecular adhesion layers in accordance with the present invention include mercaptopropyltriethyoxysilane, and other mercaptoalkoxysilanes, such as mercaptopropyltrimethoxysilane, mercaptopropyltrichlorosilane, or other chain lengths such as mrcaptohexyltriethoxysilane and other mercaptohexylalkoxysilanes, as are known in the art. Where the adhesion layer is a molecular adhesion layer, the thickness of the adhesion layer typically ranges from about 5 Å to about 50 Å.

As noted above, the protein array elements are attached to the substrate via a bifunctional organic layer (FIG. 1A, element 108) present on the oxide coated reflective metal surface of the substrate. The termini of the organic molecules of the bifunctional layer are functionalized with a reactive group that can stably attach to the substrate surface at one end and with a reactive group that can stably attach to a protein array element, optionally via an adapter, at the other end. An important feature of the organic layer reactive group is that its reaction with the corresponding functional group displayed on protein array element be sufficiently facile so that it is complete within the average lifetime of a droplet that is deposited by a robotic array spotter onto the surface. Silanes are particularly well suited to bind to dielectrics such as metal oxide surfaces, and amino groups suitable for stably binding many molecular species that can in turn stably bind to a variety of proteins or linker molecules or be further chemically or biologically modified to allow attachment. Accordingly, in accordance with one specific embodiment, a layer of an aminoalkyl trialkoxysilane, such as aminopropyl triethoxysilane (APS), trichlorosilane, trimethoxysilane, or any other trialkoxysilane is coated on the surface of the dielectric 110. In addition, other amino-silanes could also be used, for example, compounds having longer alkyl groups, such as octyl, decyl, hexadecyl, etc., or compounds having alkyoxy groups, such as one or more ethylene oxide units (e.g., 3) that may form more ordered silane layers as will be appreciated by those having skill in the surface chemistry arts. The thickness of this silane layer may be from about 3 Å to about 100 Å, more preferably about 5 Å to about 50 Å, even more preferably about 7 Å to about 20 Å. One suitable example is an APS layer that is about 7 Å thick. The amino-modified metal oxide surfaces may be further functionalized with a reactive group forming part of an adapter that will bind to a protein array element, as further described below.

In one specific embodiment of the present invention, the substrate may be composed of a glass microscope slide coated with a layer of aluminum about 1000 Å thick. The aluminum coated slide may then be coated with a layer of silicon dioxide having a thickness of about 800 Å. The thickness is chosen to roughly correspond to about ¼ the wavelength of the emission or excitation light, or a compromise between two different wavelengths, as further described in International Patent Application No. WO 98/53304, previously incorporated by reference herein. The layer thickness is hypothesized to allow constructive interference of the light due to reflection, and also may allow a standing wave to develop in the oxide layer. As the intensity of the signal correlates with the square of the amplitude, such a standing wave would yield at least 4× more signal, in addition to the signal gained by simple reflection (since there are no or greatly reduced losses of light relative to a glass slide). In practice, signal amplifications of 20–50× are observed for the mirrored slides compared to glass slides. A layer of an aminopropyl triethoxysilane (APS) about 7 Å thick is coated on the surface of the oxide.

B. Adapters

As noted above, microarrays in accordance with the present invention are composed of a substrate, an array element and, optionally, an adapter. Where used, the adapter may be composed of one or more, generally organic, molecular species, that alone or in combination form a bifunctional molecular entity through which protein array elements are stably attached to a substrate in accordance with the present invention. As will be recognized by those skilled in the art, within the parameters of being able to stably bind to an array element at one terminus and a substrate surface at the other, a vast array of potential molecules may be used to form an adapter in accordance with the present invention. In the myriad possible configurations, the adapter may be composed of one or more molecules. The molecule or molecules of the adapter may be homo- or heterobifunctional. The adapter molecules may be composed of one or a few discrete molecular species of total molecular weight generally less then about 1000 ("small molecules") or much larger proteins.

The adapter stably attaches to the organic layer on the substrate. As such, the adapter molecular entities should bind to the functional group displayed by the organic layer on the substrate surface (e.g., amino) and to a subsequently bound protein array element, either directly or via further molecular species initially attached to the substrate or to the protein of the array element. A suitable adapter may be, for example, a molecule having an activated ester at one terminus and a maleimide at the other (e.g., succinimidyl 4-(N-maleimidomethyl)-cyclohexane-1-carboxylate (SMCC)) which can react at the ester terminus to form covalent amide bonds with an amino group displayed by the substrate surface and at the maleimide terminus with exposed, reduced thiol (sulfhydryl-) groups in a protein array element.

Generally, any group that can react with the functional group (e.g., amine) on the substrate surface to form a stable (e.g., an amide) bond may be used as the substrate bound terminus of an adapter in accordance with the present invention. Examples of such molecular species that may be used in adapters include activated esters such as N-hydroxysuccinimide (NHS). In one embodiment, a homobifunctional NHS aster (bis-NHS ester) may be used as an adapter to connect a protein with exposed amines to the amine surface of the substrate. In alternate embodiments, heterobifunctional NHS ester molecules with various functional groups or other activated esters or anhydrides known by those in the art to react with amines may be used. Other potential functional groups include hydrazide, which can react to form covalent bonds with aldehyde or ketone moieties in the array element, aminooxy, which can react to form covalent bonds with ketone moieties in the array element, anhydride, aldehyde, disulfide, thiol, azide, phosphine, biotin or avidin, streptavidin, neutravidin or other altered forms of the protein avidin that bind biotin, depending upon the protein array element or another molecular species attached to the protein in the array element. Another suitable adapter species is a functionalized dextran. These species may be formed and attached to the organic functionalized substrate surface by techniques and using such other necessary molecules as would be well known to or readily ascertainable by those of skill in the chemical arts.

In one specific example, an NHS ester of biotin will attach to amines on the substrate surface to form the amide linkage at one end with the biotinyalted moiety at the other. The surface can then be treated with avidin and biotinylated proteins spotted onto that.

Other suitable adapters for attaching protein array elements to an amino-modified substrate surface include proteins, such as Protein A or G for attaching antibodies, or glutathione for attaching protein-GST fusions, described further below.

The adapter provides for the stable attachment of the array element to the solid surface. In many instances, the adapter will be attached to the substrate via the functional group displayed on the substrate surface prior to attachment of the protein array elements by a spotting technique. As noted above with respect to the substrate organic layer when no adapter is used, an important feature of the adapter is that its reaction with the corresponding functional group displayed on protein array element be sufficiently facile so that it is complete within the average lifetime of a droplet that is deposited by a robotic array spotter onto the surface. For example, if the adapter on the surface is a maleimide, a suitable corresponding group on the protein array element is a thiol and approximately 15–20 minutes at about 60% humidity are required for completion of the binding reaction before the approximately 10 nL drop evaporates. Of course, droplet lifetime varies with temperature, humidity and other conditions, allowing more or less time for the reaction to take place.

In some embodiments, the adapter may be chosen to provide for separation between the solid surface and the protein array element sufficient to facilitate interaction between the protein and the components of the analyte solution (solution with which the microarray will be contacted). For example, sufficient separation may be provided between the substrate surface and the protein array element so that the surface does not interfere with protein binding occurring (subsequently) at the protein array element. The adapter may also serve to separate the protein array elements on the surface from each other, thereby mitigating possible steric hindrance between the proteins binding on the array. A typical adapter may include a molecule having a backbone of between about 2 to about 200 atoms, preferably about 6 to about 30 atoms. The backbone may be composed of, for example, aliphatic chains (e.g., aminoalkanoic acids, such as aminohexanoic acid), ethylene oxides, sulfoxides, or "nonbinding" ("orthogonal") short peptoid or peptide elements that remain constant for each element of the array, or some combination of these components. In one embodiment, a 2-carbon adapter backbone may be used. In another embodiment, three ethylene oxides may be used. As an example, a short peptoid, being a 2-mer to 12-mer, for example a 4-mer, of methoxyethyl side chains that remain constant for each protein array element may be used A suitable peptide adapter backbone is a 2-mer to 12-mer, for example a 5-mer of glycine.

It should be recognized that the nature of the adapter may be highly variable depending on the nature of the substrate functional group and the proteins to be incorporated into the array. Some examples of suitable substrate/adapter/protein combinations in accordance with the present invention are described below in section E.

C. Protein Array Elements

As noted above, the protein array elements of the present invention are proteins that are directly or indirectly (via an adapter) bound to a solid substrate. Protein array elements may be any type of unmodified proteins or modified proteins including antibodies and fusion proteins. The protein array elements may be attached to the surface of the solid substrate by direct binding between function groups of the organic modified substrate surface and of the protein, or, more commonly, via a suitable molecular species, referred to herein as an adapter, present on the substrate surface and/or the proteins to facilitate the attachment of the array element to the surface of the solid substrate.

As mentioned above, the number of different types of protein array elements present on the surface of the array is at least two. By "different", it is meant that the proteins of different array elements are not the same. While the number of different species of protein array elements present on the surface of the array is at least 2, at least about 10, at least about 50, or at least about 100, it is typically much higher, generally being at least about 1,000 usually at least about 5,000 and more usually at least about 10,000. The number may be as high as 500,000 or higher, but typically does not exceed about 100,000 and usually does not exceed about 50,000

D. Surface Chemical Blocking

After spotting of the array elements onto the array substrate (chip), the remaining, uncoated surface of the chip may be functionalized with a molecule that displays a hydrophilic terminus. These hydrophilic termini are anticipated to reduce or eliminate non-specific binding of proteins in the complex mixture. The hydrophilic portion may consist of alcohols, sulfoxide, carbohydrates, acrylamides, with hydrophilic termini such as alcohols, carbohydrates, amino acids, sulfoxides, acrylamides, and ethers or other low-protein binding group. The hydrophilic display molecule is anchored to the chip in the same manner as the protein array elements that have already been spotted. For example, chips may be chemically blocked with cysteine, mercaptoethanol or other suitable hydrophilic thiol. The chips may also or alternatively be blocked with protein such as 2% BSA/PBS, 10% non-fat dry milk or 1% casein for at least 1 hour, rinsed with water and dried. Other possible blocking agents are noted above. The blocking agents may be applied to the chips in ways well known to those of skill in the art, such as by dipping the chips in a solution of a blocking agent, by painting the surface of the chips with a blocking agent solution, or by spin-coating.

Alternatively, the surface regions surrounding the protein array elements may be modified with polymeric or oligiomeric chemical blocking agents so as to minimize background non-specific binding of proteins, allowing complex samples (e.g., lysates or serum) to be examined in a single step. The surface may be blocked chemically following spotting of the protein array elements with a hydrophilic polymeric or oligomeric molecule that reduces or eliminates non-specific protein binding to the array. As opposed to conventional protein blockers such as BSA and casein, the polymeric or oligomeric chemical blocker is a synthetic molecule that may be used alone or together with a protein blocker. In a specific embodiment, a chemical blocker and a protein blocker may be used together, e.g., chemical block followed by protein block in sequence or chemical block mixed with protein block and then applied to the array surface after spotting. Polymeric chemical blocks such as PEG modified at its termini to bind to functional groups displayed on the substrate surface have been found to be more effective for resolving specific binding of proteins from a complex mixture on a protein array chip. The polymeric or oligomeric chemical blocking agent may be attached to the array by dipping the slide into the blocking agent after spotting.

For example, in a specific embodiment, the chemical blocking agent is a polyethylene glycol (PEG) analog, modified at at least one terminus so that it will react with and bind to the organic functionalized substrate surface not occupied by array elements. For example, the chemical blocking agent for a maleimide functionalized surface may be a thiol-modified polyethylene glycol (PEG). One specific example is a dithiol-modified PEG (SH-PEG-SH), for example having a molecular weight of about 3400–5000 (for example, commercially available from Shearwater Polymers). The blocking agent may be applied with casein after the array element spotting is completed, as described below, or in a step beforehand. The possible functionalities for the blocker termini are the same as those for the adapters noted above, e.g., could be biotin, amine, activated ester, etc.

Another type of chemical blocking in accordance with the present invention is provided by well-defined, monodisperse oligomers of N-substituted glycines (peptoids) derivatized with hydrophilic side chains that can be readily attached to a variety of surface functionalities. Suitable side chains may have one or more ethylene glycol units, or may also be composed of hydroxyls, sulfoxides, or other hydrophilic groups (such as described above) that resist protein adsorption. These molecules are designed to resist protein binding and would be interspersed with the specific protein binding molecules of the protein array (e.g., antibodies, fusion proteins, etc). These chemical blockers may be optimal for high density packing of the protein-resistant moieties and thus provide improved resistance to non-specific protein binding (NSPB). These peptoid chemical blockers and there synthesis and application are described further below with reference to FIG. 3.

E. General Features of the Array

Typically, the array is characterized by having a plurality of protein spots on a solid substrate, where each spot is characterized by having one or more, usually a plurality, of identical proteins bound to the support surface. The number of distinct spots on the surface of the array may or may not be the same as the number of different proteins on the array, e.g., the same protein may be presented in two or more spots on the array surface. In one embodiment, each protein is presented in duplicate in the array. Depending on the nature of the proteins of the array elements, the size of the support surface, the methods of fabrication and the intended use of the array, the number of distinct spots on the array surface may vary greatly. Where the support surface has the dimensions of a standard microscope slide (about 3"×1"), the number of spots on the support surface will typically be at least about 3,000, usually at least about 6,000 and more usually at least about 10,000–50,000. The number may be as high as 100,000 or higher, but typically does not exceed about 75,000 and usually does not exceed about 50,000.

The diameter of each spot will typically range from about 100 μm to about 300 μm, usually from about 200 μm to about 300 μm. The space between any two given spots will generally be between about 1 μm and about 50 μm or 100 um. The density of the spots generally ranges from about 1 to about 5,000 spots/cm$^2$, usually from about 100 to 2,000 spots/cm$^2$. Typically, the spots are arranged across the surface of the spacer layer in the form of a pattern. The pattern may be in the form of organized rows and columns of spots, e.g., a grid of spots, across the substrate surface, a series of curvilinear rows across the substrate surface, e.g., a series of concentric circles or semi-circles of spots, and the like. To further increase density, the spots may also be hexagonally arranged. Still other arrangements of spots are within the scope of the present invention.

Figure 2C:
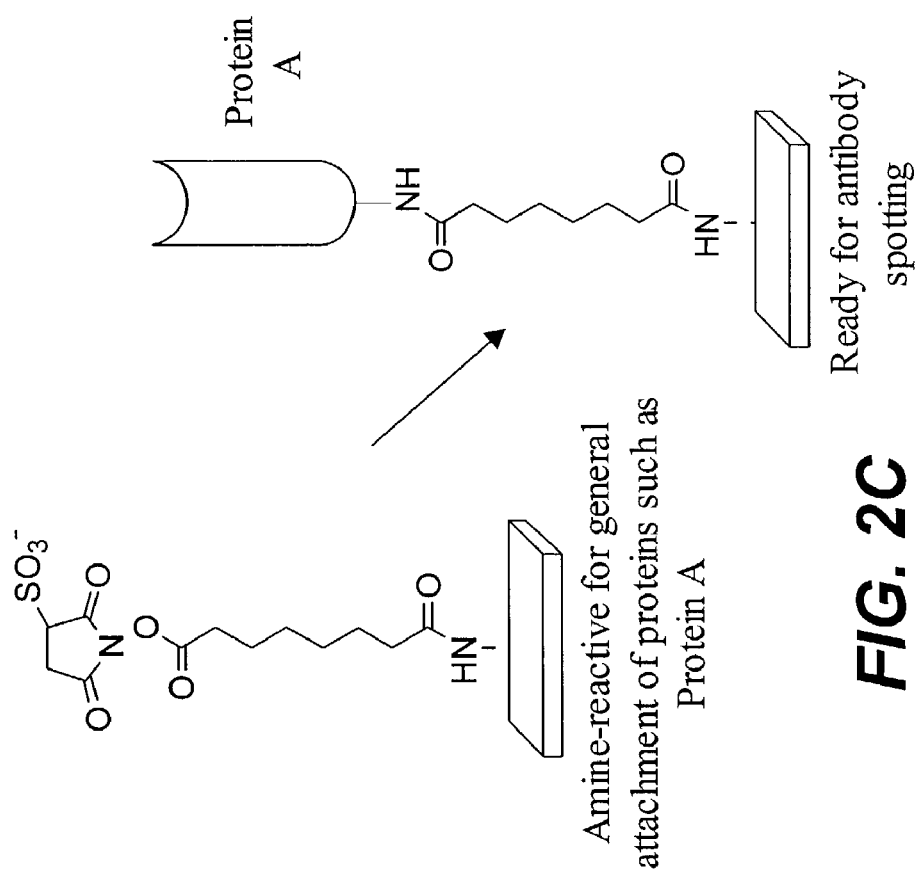

As noted above, the attachment of the protein array elements to the substrate may take a variety of forms. In most instances, the protein array elements will be attached to the substrate via an adapter. However, in some instances in accordance with the present invention the attachment may occur directly without the use of an adapter. For example, as depicted in FIG. 2A, amines on the substrate surface may react directly with activated carboxylic acid (converted to esters by standard protein chemistry techniques) groups in protein array elements. This technique may be particularly useful for small proteins without thiol groups (cysteine residues) which are otherwise commonly used for attachment of proteins in accordance with the present invention.

There are many modes of attachment of protein array elements to substrates via adapters in accordance with the present invention. Some examples are described here and in further detail below.

Figure 2B:
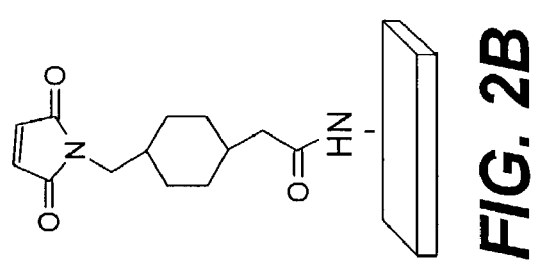
Figure 2A:
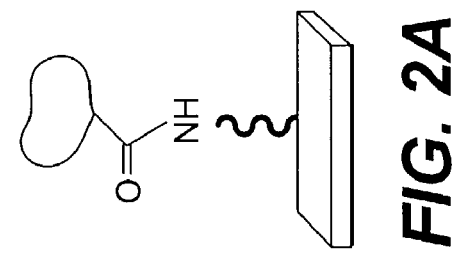

As depicted in FIG. 2B, amine functionalized substrate surfaces can be derivatized with maleimide groups by reacting amine groups displayed on the substrate surface with heterobifunctional crosslinkers. One example is a molecule that has an N-hydroxysuccinimide (NHS) ester at one terminus, and a maleimide group at the other. The NHS ester reacts with the amines on the substrate to produce a maleimide functionalized slide.

Proteins containing exposed, reduced thiol groups can be spotted onto such a slide to produce covalently bound protein microarrays. Reduced whole proteins such as antibodies can also be attached in this manner where disulfide groups in the Fc region of an antibody can be reduced to a thiol available for reaction with the maleimide of the adapter without affecting the activity of the antibody's variable region (for example, as described in Levison, M. E., et al, (1969), Experentia, vol 25, 126–127 and Blauenstein, P., et al, (1995), Eur. J. Nuclear Med., vol 22, 690–698).

As depicted in FIG. 2C, amine functionalized substrate surfaces can be derivatized with an activated ester by reacting amine groups displayed on the substrate surface with a homobifunctional crosslinker. One example is a bis-NHS ester molecule. The NHS ester at one terminus of the adapter reacts with the amines on the substrate to produce an NHS ester functionalized slide. Proteins, for example Protein A, containing exposed amine groups can be spotted onto such a slide to produce covalently bound protein microarrays.

As depicted in FIG. 2D, amine functionalized substrate surfaces can be derivatized with biotin by reacting the amine groups with activated biotin molecules. One example is a molecule that has an NHS ester at one terminus and a biotin group at the other. The NHS ester reacts with the amines on the slide to produce a biotinylated surface. Such a surface can be used to attach, via robotic spotting, a variety of protein-avidin conjugates for displaying protein arrays.

As depicted in FIG. 2E, biotinylated slides, such as described above with reference to FIG. 2D, can also be coated with a layer of avidin, streptavidin or any other avidin analog, simply by dipping the slide in the protein solution. Because of the tetrameric nature of the avidin protein, sites are still available even after the avidin has bound to the biotinylated slide, therefore, biotinylated proteins may then be spotted on the avidin-treated slides.

Avidin-treated slides, such as described above with reference to FIG. 2E, may be further derivatized by dip-coating into a variety of biotinylated protein solutions. One example is to dip coat the avidin coated slides into a solution of Protein A or Protein G. In this manner, a Protein-A/G derivatized surface is generated. These may be used for spotting down antibodies in a highly oriented and specific manner. The Fc portion of the antibody is known to bind to Protein A or Protein G. Therefore, the Fab fragments are freely displayed at the surface. Or alternatively, the avidin-treated slides would be spotted with biotinylated proteins.

Also, Synthetic mimics of the avidin-coated slides may be used. In this motif, oligomers of comparable bulk and thickness to avidin are dip-coated onto the amine-derivatized substarte slides. The oligomers are heterobifunctional such that one end reacts with the amines on the surface, while the other end is activated for binding spotted proteins (for example, with maleimide or thiol). The large area occupied by the oligomer is anticipated to mimic the display motif of avidin, in that the proteins are displayed at a significantly lower density compared to direct attachment of proteins to the solid support.

Figure 2F:
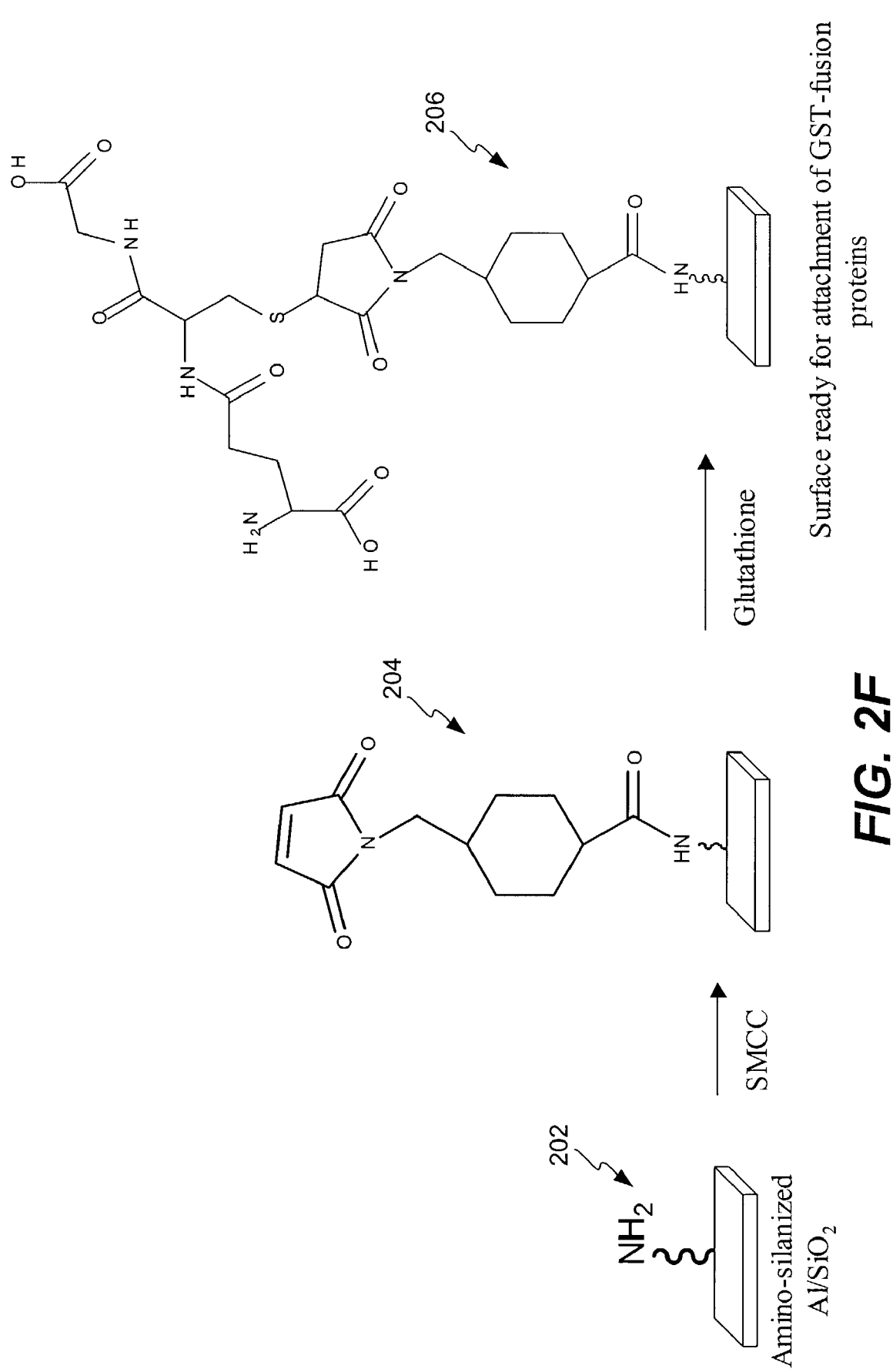
FIG. 2F schematically depict a mode of binding a fusion protein array element to a solid support in accordance with specific embodiments of the present invention.

As depicted in FIG. 2F, in another embodiment, amine functionalized substrate surfaces (202) can be derivatized with an adapter that is reactive to a fusion protein. For example, expression of proteins as GST-fusions is often desirable because the GST (Glutathion Synthase Transferase, 30 kd) provides a handle with which to purify the expressed proteins, using glutathione columns. In addition, the GST aids in the solubilization of proteins to a much greater extent compared to other fusion systems such as His-6. Finally, the GST fusions can be expressed at lower temperature, further aiding solubility and proper folding of the expressed proteins. Suitable adapters may then have a non-substrate bound functional group that binds to a fusion protein. In the case of GST-protein fusions, a glutathione group may be used. The glutathione terminus may be formed by reacting amine groups displayed on the substrate surface with heterobifunctional crosslinkers. One example is a molecule that has an N-hydroxysuccinimide (NHS) ester at one terminus, and a maleimide group at the other. The NHS ester reacts with the amines on the substrate to produce a maleimide functionalized slide (204). A free thiol on the glutatione is available to react with the meleimide to provide a glutathione functionalized slide (206). Protein-based functional domains expressed as GST fusions can be readily spotted onto the glutathione displaying slides to generate arrays in accordance with the present invention.

An alternative fusion protein adapter strategy involves avidin-treated slides, such as described above with reference to FIG. 2E, which may be be functionalized with biotinylated glutathione. In this motif, a glutathione molecule derivatized at its sulthydryl with a spacer that has a biotin at its other terminus may be used. Dip coating the avidin coated slides would result in an substrate surface that is derivatized with glutathione that would be used for spotting down GST-fusions.

As will be readily apparent to those of skill in the surface chemistry arts, there are a myriad possible configurations for adapters in accordance with the present invention and the invention is in no way limited the specific embodiments described above and the examples provided herein which are provided to clarify the disclosure of the invention In summary, protein microarrays in accordance with the present invention incorporate a type of solid substrate not previously used for protein arrays, namely an oxide coated reflective metal functionalized with a reactive group to facilitate attachment of proteins to form an array. A specific example is an aluminum coated glass slide with a further coating of silicon dioxide and an amino-silane layer so that the substrate displays an amino groups for binding of protein array elements. The proteins array elements may be attached directly, or for a broader range of possible protein array elements, indirectly via a myriad different possible adapters, to form the protein microarrays of the present invention.

2. Methods of Making the Protein Arrays of the Subject Invention

The arrays of the subject invention may be prepared using any convenient protocol. One protocol of interest involves 1) the procurement of a solid support having a surface activated for binding of a protein array element; and 2) contact of two or more different protein array elements with the support surface under conditions such that the protein array elements become stably associated with the support surface. Many aspects of substrate and array fabrication applicable to the present invention are described in application Ser. No. 09/874,091 and corresponding International Patent Application PCT/US01/18066, incorporated herein by reference for all purposes.

A. Substrate Fabrication

The solid support may be fabricated using any convenient methodology, which will vary depending the particular nature of the solid support. In accordance with one embodiment of the invention, a solid support, e.g., glass, plastic or metal, is coated with a layer of a reflective metal, e.g., aluminum, gold, silver, platinum, copper, titanium, or chromium. To prepare a solid support of glass coated with a alumimum, for example, the surface of the glass is coated with a thin layer of aluminum in a thickness as described above, e.g., about 1000 Å. The metal layer may be deposited on the substrate surface using any convenient protocol, where suitable protocols include e-beam deposition, vapor deposition, sputtering, and the like, and are known to those of skill in the art. See e.g., Moteshari et al., J. Am. Chem. Soc. (1998) 120:1328–1336; Bain et al., J. Am. Chem. Soc. (1989) 111:7155–7164; Lee et al. Langmuir (1998) 14:6419–6423; Folkers et al., Langmuir (1992) 8:1330–1341. Where convenient, an adhesion metal layer may be present between the metal layer and the substrate, where adhesion metals of interest include titanium, chromium, and the like, deposited in a thickness as described above. It is also possible the reflective metal layer may be the surface of a metal solid support. For example, an aluminum slide may be used.

Following the preparation of the reflective metal surface, an oxide layer having the composition and thickness described above is formed on the metal layer For example, about 800 Å of silicon dioxide on an aluminum layer. The oxide may formed by any suitable technique, such as by e-beam or sputtering deposition on top of the metallic layer. Metal substrate surfaces may be also be oxidized, for instance by thermal or chemical treatment. For example, aluminum may be oxidized electrochemically, thermally or chemically (e.g., with $H_2O_2$), as is well known in the art. An oxide may also be present as a native thin layer, such as occurs with aluminum.

The metal oxide may then be functionalized with a heterobifunctional silane, such as described above, e.g., aminopropyl triethoxysilane (APS), to so that the surface displays a functional group, in this case amine, suitable for the direct or indirect binding of proteins, including protein array elements. Ideally the APS is deposited in the vapor phase using a vacuum oven, as described below in Example 1.

Aluminum/oxide/APS coated slides are also commercially available from Amersham-Pharmacia, Amersham, England (and described in International Patent Application No. WO 98/53304).

In some embodiments functionalized organic molecules that form ordered monolayers. The termini of the organic molecules are functionalized with a reactive group that can attach to a suitable reactive group of a protein array element or adapter, such as described further above and exemplified below. Suitable terminal groups may be, for example, maleimide, hydrazide, aminooxy, an activated ester such as N-hydroxysuccinimide, anhydride, aldehyde, disulfide, thiol, azide, phosphine, biotin, avidin, or an avidin analog or mimic.

In one embodiment, functionalized aluminum oxide slides may be used. Aluminum metal may be deposited by e-beam deposition onto a clean glass substrate. The aluminum is then overcoated by silicon dioxide ($SiO_2$) or silicon monoxide in a thickness that is the same or thinner than ¼ the wavelength of the emission or excitation light as described above. Oxide thicknesses of about 600 to 1000 Å, for instance 800 Å, may be used for the standard Cy5 (650/670 nm) and Cy3 (550–570 nm) dyes as these eliminate the need for thinning the oxide prior to performing binding experiments. The range of 800–950 works well for Cy5 and Cy3 dyes and can be adjusted and optimized for each dye if others are to be used. The aluminum/oxide surface may be treated with a amino-modified silane. For example, aluminum slides freshly coated with a 800–1,400 Angstrom layer of silicon dioxide, may be dipped immediately into a bath of 3%–40% aminopropyl triethoxysilane in isopropanol, that has been previously filtered through an 0.2 uM filter membrane, and silanized for up to 1 hour, followed by rinsing and drying. Vapor phase is preferred. Alternatively, as noted above, aluminum slides coated with silane (APS) are available from Amersham-Pharmacia, Amersham, England. In some cases, such commercially available slides may require thinning of the oxide layer to between about 200 Å and about 1,000 Å, more particularly about 800 Å, prior to performing a binding experiment to improve signal-to-noise ratios. If thinning of the oxide on commercially available slides is required, the oxide may be "etched" or thinned to around 800 angstroms by incubating slides at 60 C in SSC buffer (NaCl and NaCitrate).

The final amino-modified Al surfaces may be functionalized with a heterobifunctional activated ester to render a surface that presents appropriate functional groups. The silane may also be vapor deposited or spin coated. For example, a 1–10% (e.g., 5%) solution of silane in a volatile solvent such as isopropanol, methanol, THF may be prepared. The slides may be spun at 1,000–8,000 rpm (e.g., 5,000 rpm) to provide an even deposition of the silane. Then, a heterobifunctional molecule (e.g., succinimidyl 4-(N-maleimidomethyl)-cyclohexane-1-carboxylate (SMCC or LC-SMCC)), that is an activated ester on one end and a maleimide on the other, is contacted with the amino group to create a maleimide-terminated surface. Other heterobifunctional cross-linkers or combinations of molecules could also be used, as described above (e.g., a long ethylene oxide spacer (e.g., 2–4 units) between an NHS ester on one end, and a biotin or maleimide on the other end.

Further in accordance with this embodiment, it has been found that amplification of the fluorescent signal used in assays conducted with microarrays in accordance with the present invention may be enhanced by using functionalized and spotted aluminum slides with an oxide layer thickness of about 200 Å to about 900 Å, preferably about 800 Å. Slides with initially thicker oxide layers may be etched, for example with an etch solution of about 0.1–0.2% SDS/5× SSC (0.75 M NaCl/0.085 M sodium citrate) and optionally 5 mM EDTA may be applied at about 50–80 degrees, preferably about 60° C. for about two to four hours. As noted above, manual deposition of a silicon dioxide layer of a suitable thickness may eliminate the need for the thinning of the slide.

B. Array Fabrication

Following preparation of the substrate, as described above, two or more different proteins of interest that are to be bound to the surface as array elements to produce the array are contacted with the functionalized substrate surface. By contact is meant that the binding agents are brought into proximity with the surface such that they become substantially stably attached or bound to the surface of the substrate layer.

In contacting the protein array elements with the substrate surface, any convenient means for contacting the surface with the proteins which results in the desired pattern of protein array element spots, as described above, may be employed, e.g., by spotting. Generally, an aqueous solution including an agent to reduce the evaporation rate (e.g. buffer/glycerol (such as 75/25 tris-buffered saline/glycerol, or the like) of the protein is employed during contact where the solution may comprise one or more components in addition to water and the protein, e.g., buffering agents, salts, and the like. When a higher percentage of buffer is used in the aqueous solution, the drop sizes can be smaller because of the higher surface tension of the solution. Drop size (and therefore density) may be controlled to some extent in this manner. Typically, contact is achieved by depositing solutions of the different protein array elements onto discrete locations of the support surface, such that each different type of protein array element is deposited onto its own unique location on the substrate surface.

The binding agents may be deposited onto the support surface using any convenient means, e.g., by pipetting. A number of devices and protocols have been developed for depositing aqueous solutions onto precise locations of a support surface and may be employed in the present methods. Such devices include "ink-jet" printing devices, mechanical deposition or pipetting devices and the like. See e.g., U.S. Pat. Nos. 4,877,745; 5,338,688; 5,474,796; 5,449,754; 5,658,802; 5,700,637; and 5,807,552; the disclosures of which are herein incorporated by reference. Robotic devices for precisely depositing aqueous volumes onto discrete locations of a support surface, i.e., arrayers, are also commercially available from a number of vendors, including: Genetic Microsystems; Molecular Dynamics; Cartesian Technologies; Beecher Instruments; Genomic Solutions; and BioRobotics. Alternatively, bubble jet technology recently described by Okamoto, Suzuki and Yamamoto, *Nature Biotechnology,* vol. 18 (April, 2000), 438, may be used.

As noted above, an important feature of a process in accordance with the present invention is that the reaction between the protein array element, option adapter, and the substrate surface must be sufficiently facile so that it is complete within the average lifetime of a droplet that is deposited by the robotic array spotter onto the surface. For example, if the surface is functionalized and displays a maleimide as part of an adapter, a suitable anchoring group is a thiol and approximately 15–20 minutes at about 60% humidity are required for completion of the binding reaction. As noted above, other surface display/anchor combinations are possible, including those forming stable, yet non-covalent bonds, such as avidin and biotin.

C. Blocking the Chip

After spotting of the protein array elements onto the array substrate (chip), the remaining, uncoated surface of the chip may be functionalized with a chemical blocker, a hydrophilic generally polymeric or oligomeric molecule that reduces or eliminates non-specific protein binding to the array. As opposed to conventional protein blockers such as BSA and casein, the chemical blocker is a synthetic molecule that may be used alone or together with a protein blocker. In a specific embodiment, a chemical blocker and a protein blocker may be used together, e.g., chemical block followed by protein block in sequence or chemical block mixed with protein block and then applied to the array surface after spotting. Chemical blocks such as PEG modified at it termini to bind to functional groups displayed on the substrate surface have been found to be more effective for resolving specific binding of proteins from a complex mixture on a protein array chip. The chemical blocking agent may be attached to the array by dipping the slide into the blocking agent after spotting.

As noted above, in a specific embodiment, the chemical blocking agent is a polyethylene glycol (PEG) analog, modified at at least one terminus so that it will react with and bind to the organic functionalized substrate surface not occupied by array elements. One specific example is a dithiol-modified PEG (SH-PEG-SH). The blocking agent may be applied with casein after the array element spotting is completed, as described below, or in a step beforehand. The possible functionalities for the blocker termini are the same as those for the adapters noted above, e.g., could be biotin, amine, activated ester, etc.

Another type of chemical blocking in accordance with the present invention is provided by well-defined, monodisperse oligomers of N-substituted glycines (peptoids) derivatized with hydrophilic side chains that can be readily attached to a variety of surface functionalities. Suitable side chains may have one or more ethylene glycol units, or may also be composed of hydroxyls, sulfoxides, or other hydrophilic groups (such as described above) that resist protein adsorption. These molecules are designed to resist protein binding and would be interspersed with the specific protein binding molecules of the protein array (e.g., antibodies, fusion proteins, etc). These chemical blockers may be optimal for high density packing of the protein-resistant moieties and thus provide improved resistance to non-specific protein binding (NSPB).

These chemical blocker oligomers may be prepared using the submonomer peptoid synthesis method described in application Ser. No. 09/874,091 and corresponding International Patent Application PCT/US01/18066, incorporated herein by reference for all purposes. Peptoids may be synthesized using robotic solid-phase synthesis techniques, such as those developed by Chiron Corporation of Emeryville, Calif. The composition of the peptoids can be controlled by the nature and arrangement of the selection of the hydrophilic R groups (e.g., alcohols, sulfoxide, carbohydrates, acrylamides, with hydrophilic termini such as alcohols, carbohydrates, amino acids, sulfoxides, acrylamides, and ethers or other low-protein binding group, as noted above) on the amine submonomers (bromoacetic acid and substituted amines) used in the peptoid synthesis.

As noted above, for a peptoid-based chemical blocking agent, the N-substitutions are moieties that are known to be highly resistant to non-specific protein binding, such as ethylene oxide, sulfoxide, hydroxyl, etc. The N-terminus can be modified with a variety of surface immobilization groups such as biotin, thiol, hydrazide, aldehyde, epoxide, triethoxysilane, etc., as previously described.

The length of the peptoid blocker can be readily varied from about 2–100, where 15–30 is practical and would result in pure materials without a subsequent purification step. The length of the side chains can be varied from between 1–10, with 1–5 providing facile coupling to the peptoid backbone. In addition, both the C-terminus and N-terminus may be modified with a variety of chemical ligation reagents. Molecular weights can be in the range of 500–5000, generally around 2000–3000.

After synthesis has completed, the NSPB-peptoid may be cleaved using conventional cleavage reagents such as 95% TFA/5% water. This method can yield NSPB-peptoids in multi-gram quantities which can readily be used to coat microarray slides in fairly large batches (e.g. 20 slides at a time, using 200 mL of coating solution). In the course of a microarray binding experiment, the NSPB-peptoid may be incorporated directly into a protein blocking solution such as casein, non-fat milk, BSA, etc. Alternatively, it may be used as a separate coating step before or after protein blocking. The mode of attachment of the microarray element (e.g., antibodies or protein fusions) to the surface would likely determine the motif of NSPB-peptoid used. For example, if biotinylated proteins are attached via robotic spotting to avidin-coated slides, then a biotinylated NSPB-peptoid would be used as the coating to block NSPB.

Figure 3:
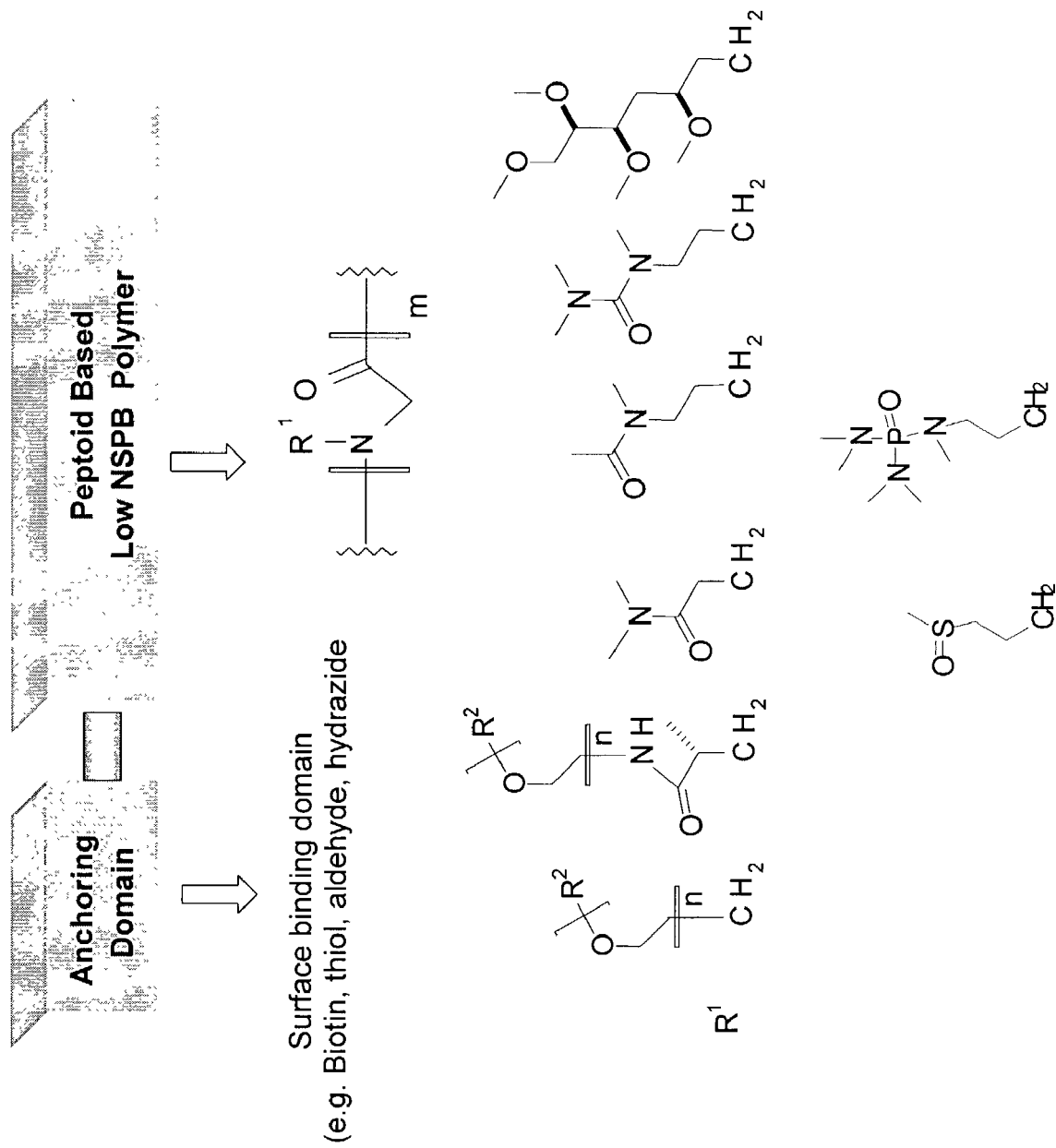
FIG. 3. illustrates a peptoid-based chemical blocking agent for inhibiting non-specific protein binding (NSPB) in accordance with the present invention.

FIG. 3. illustrates a peptoid-based chemical blocking agent in accordance with the present invention. The peptoid-based polymer chemical blocker is designed to stay hydrated and resist the nonspecific binding of proteins. In the figure, $R^1$=H or Me, m=2 to 100, n=1 to 10. The "anchoring domain" refers to the mode of attachment to the substrate surface, generally, an adapter, as described herein.

D. Summary

Figure 4:
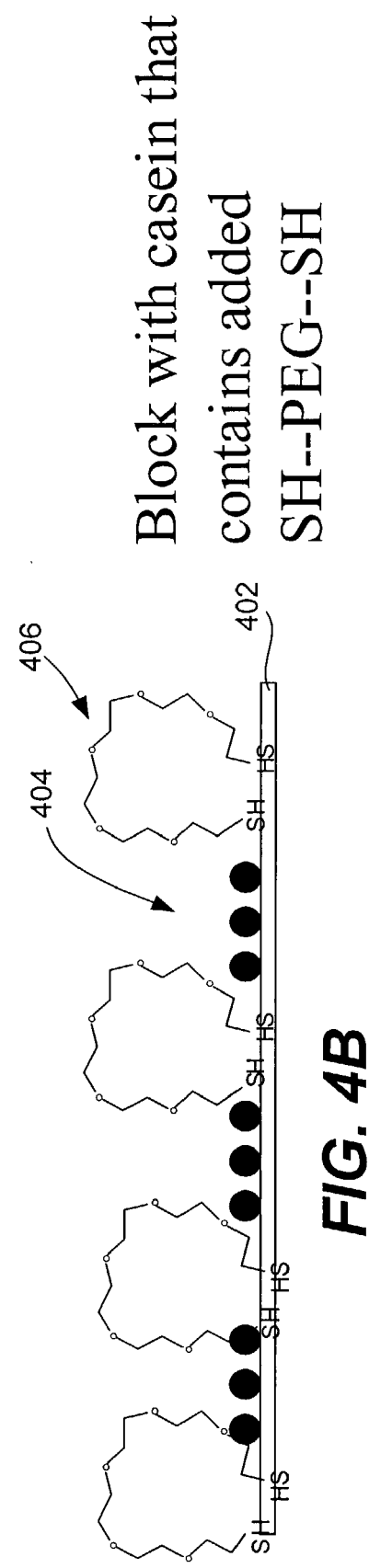
FIG. 4A–4B schematically depicts the formation of a blocked protein array for conducting a differential protein binding assay in accordance with one embodiment of the present invention using a functionalized PEG.

FIGS. 4A and 4B briefly illustrate processes for making protein arrays for some embodiments of the invention in accordance with the procedures described above. In FIG. 4A, a planar substrate 402 with an aluminum/oxide surface is provided. The surface is prepared for binding by applying a functionalized amino modified silane layer (e.g., APS), as described above. Protein array elements 404 with reactive group functionality complementary to the substrate surface layer binding functionality (e.g., reduced thiols on the case of maleimide) are spotted onto the substrate. As shown in FIG. 4B, once binding of the protein array elements 404 is complete, a chemical blocking agent 406, in this case a dithiol-modified PEG (SH-PEG-SH) for the maleimide functionalized surface is applied to the surface of the substrate where no protein-binding agent is bound.

3. Methods of Using the Protein Arrays of the Subject Invention

The subject arrays find use in a variety of different applications in which binding events between the surface bound proteins of the array and analyte(s) of interest in a test sample are detected. In other words, the arrays of the subject invention find use in binding assays. In such applications, the support bound protein generally acts as a "target" for the analyte "probe" in the test sample. The analyte probe is typically labeled, e.g., where the label may be a directly detectable label (e.g., radioactive isotope, fluorescent label, chemiluminescent label, etc.) or an indirectly detectable label (e.g., member of a signal producing system, such as a ligand for a labeled antibody, where the label may be enzymatic which converts a substrate to a chromogenic product, etc., where the labeled antibody may be a secondary labeled antibody) so that binding events may be readily detected.

In particular, arrays in accordance with the present invention are useful in performing proteomic analyses of complex protein samples. As used herein, proteomics is the separation and/or quantitation and/or identification of one or more proteins in a sample. The sample may be derived from a cell (e.g., the cell's cytosol, membrane or extra-cellular proteins), tissues (e.g., dissected or laser-microdissected), body fluids (such as urine, blood spinal fluid) or any other sample containing proteins. The results of such separation/quantitation/identification may produce novel protein targets for drug screening, proteins for diagnostics, or novel synthetic ligands for assays or protein purification. The arrays may very effectively be used in differential protein binding assays. For example, two (or more)-color fluorescent labeling of complex protein mixtures, and the analysis of differential protein binding to the array by fluorescence imaging may be conducted. As described below, the arrays may be used in conjunction with other techniques to identify, sequence and structurally characterize differentially expressed proteins or peptides of interest. The arrays may be run in parallel with DNA arrays and the differential binding results compared to identify correlations between gene activity and protein expression. Also, mixed arrays, wherein the molecules making up an array includes antibodies, etc. may be prepared and used to conduct binding assays.

A variety of techniques can be used to conduct differential binding assays using arrays in accordance with the present invention ("proteomic microarrays"). Some of these techniques, as used in embodiments of the present invention, are described below:

A. Protein Labeling

Complex protein samples are labeled using standard techniques, many of which have been developed for 2-D gel analysis of protein mixtures. For example, sample A may be labeled with an amine reactive Cyanine 3 dye ("Cy 3") ($\lambda_{ex}$=550 nm/$\lambda_{em}$=570 nm), and sample B is labeled with an amine reactive Cyanine 5 dye (Cy 5) ($\lambda_{ex}$=650/$\lambda_{em}$=670 nm) (dye reagents available from Amersham-Pharmacia). Samples A and B may be, for example, from normal or diseased, treated or untreated, etc., tissues or cell lines, respectively. The unreacted dye may be separated from the labeled protein using standard methods such as gel filtration, dialysis, etc. Of course, as noted above, a variety of different labels, as are well known to those of skill in the art, including, but not limited to, tetramethylrhodamine-isothiocyanate (TRITC), fluorescein-isothiocyanate (FITC), and succidimidyl ester derivatives, thereof, or any other dye molecule that may be reacted to proteins via amino acid side chains such as amine side chains (lysine), thiol side chains (cysteine) or other suitable functional group.

B. Binding Assay and Chip Readout

Labeled protein samples are incubated with the protein microarray chip for periods of time, and under a variety of conditions of pH, salt content and temperature anticipated to modulate the affinity of various proteins to the elements of the array. Generally, the samples are contacted with the microarray by introduction of an appropriate volume of the fluid sample onto the array surface, where introduction can be flooding the surface with the sample, deposition of the sample onto the surface, e.g., with a pipette, immersion of the entire array in the sample, and the like. In many embodiments, the solution is deposited onto the surface and then sandwiched beneath a cover slip or in a sealed chamber.

For example, a 25 µL–100 µL (typically 50 µL) aliquot of each probe solution may be applied to the surface of a typical microscope slide-sized chip, and a cleaned coverslip placed on top, forming a sandwich of the probe solution on the chip surface. The protein solutions may then be co-incubated with the chip for at least 1 hour, or overnight. After incubation, the coverslip is removed and the chip is washed, for example, in 1×PBS/0.05% Tween or other suitable buffer containing surfactant. The chip may be washed using a variety of conditions that decrease or increase stringency. These conditions can again be customized to allow, for example, retention of only the most strongly bound proteins. Or, as the case may warrant, less stringent washing may be used to allow visualization of comparatively weaker bound proteins. The choice is likely to be determined by the complexity and diversity of the array that is displayed on the chip and the nature of the protein mixture. The washed chips are then dried, for example, under a stream of Argon or Nitrogen.

After suitable washing, the chip is read in an array scanner, such as are well known in the art. The ratio of Cy 3 to Cy 5 for each spot is determined using commercially available software. Spots that show a ratio considerably greater than or less than one are observed, and deemed to be "differential".

Figure 5:
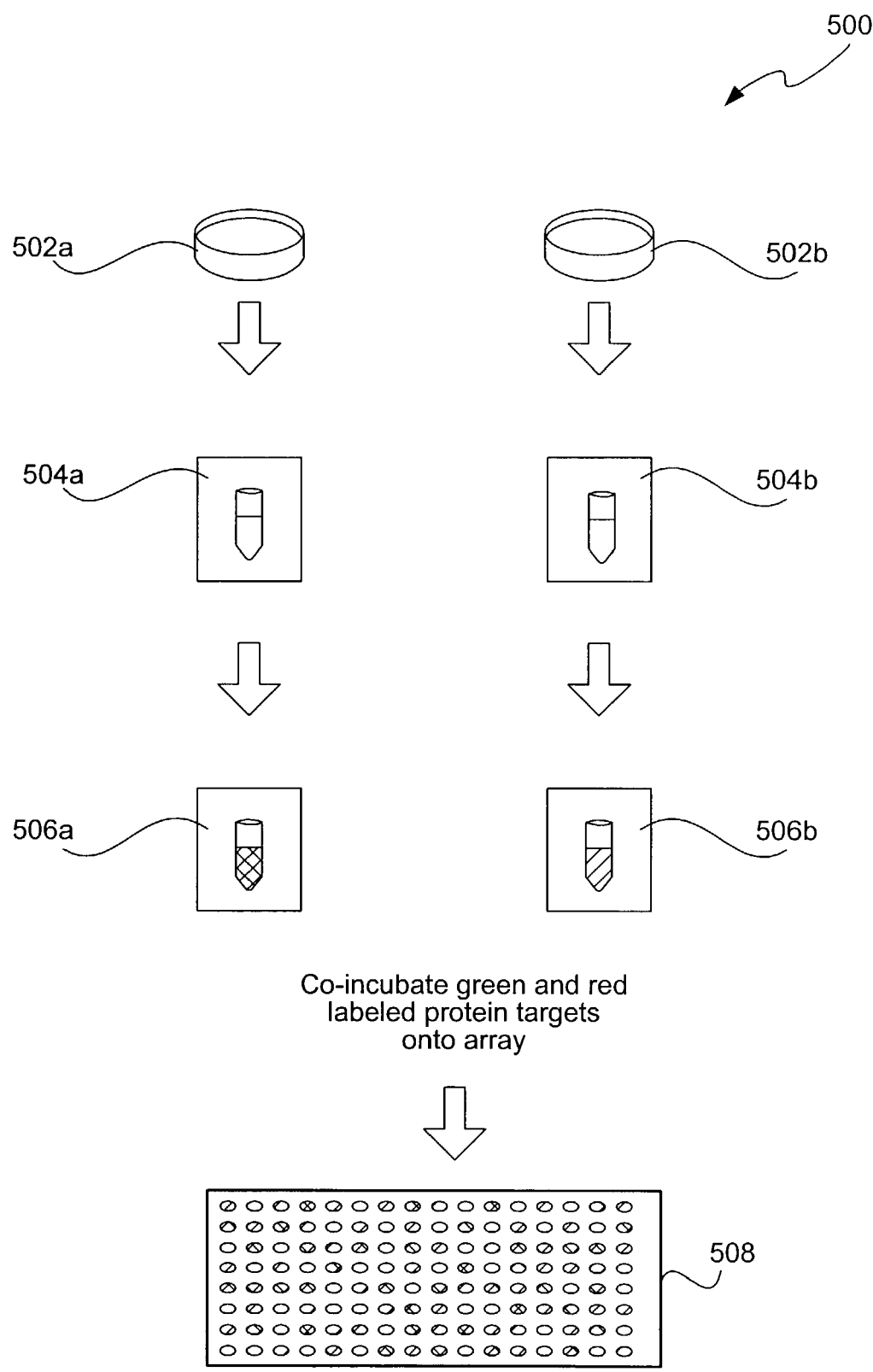
FIG. 5 briefly illustrates a process for conducting a differential proteomic binding assay using protein arrays in accordance with one embodiment of the present invention.

FIG. 5 briefly illustrates a process for conducting a differential proteomic binding assay using protein arrays for one embodiment of the invention in accordance with the procedures described above. In FIG. 5, the process (500) begins with the procurement of two biological samples to compare, e.g., an "untreated" cell line 502a and a "treated" cell line 502b. Cell lysates 504a,b are isolated from the cell line samples. The lysates are labeled, for example, the "untreated" cell lysate 504a is labeled with a fluorescent green dye while the "treated" cell lysate 504b is labeled with a fluorescent red dye. The labeled samples 506a,b are then co-incubated on a protein array chip 508 in accordance with the present invention, e.g., an array of antibodies. The protein in the samples can either be denatured or native. For example with the addition of 1–2% SDS the proteins in the samples may be denatured and clusters or hydrophobic interactions minimized or eliminated. Alternatively, the clusters, which may be important in elucidating protein-protein binding pathways, and proteins may be kept in their native states and the results studied. The chip is then read in an array scanner.

Of course, a variety of alternative assays are possible using the arrays in accordance with the present invention. For example, unlabeled protein or mixture (such as a cell lysate or serum sample) may be applied to the array and the detection may be accomplished by a secondary labeled protein, such as a secondary labeled antibody.

C. Post-Array Processing: Protein Isolation, Purification and Identification

Once a protein or set of proteins is determined to be differential between samples A and B or responsive to a particular stimulus, it can be isolated by preparing chromatographic supports composed of the same protein identified on the chip. Protein-based chromatographic supports, their preparation and their use are well known in the art.

Once the protein is isolated, it's sequence can be determined using standard techniques such as MALDI. Also, trypsin digests can be analyzed by tandem MS techniques.

Figure 6:
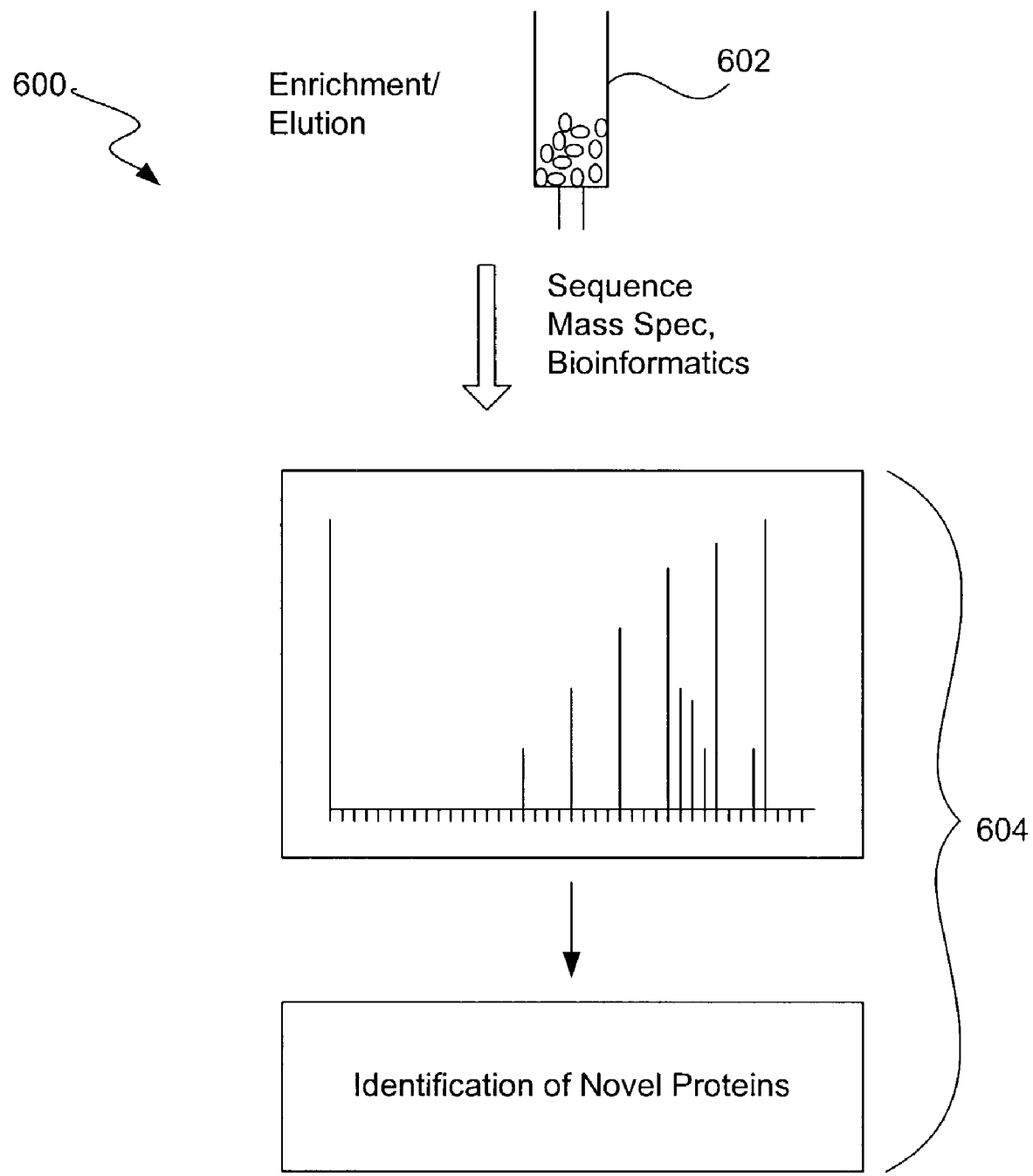
FIG. 6 briefly illustrates aspects of post-array processing in accordance with one embodiment of the present invention.

FIG. 6 briefly illustrates aspects of post-array processing in accordance with the procedures described above and below. In FIG. 6, the process (600) begins with the preparation of chromatographic separation columns 602 using proteins, identified as of interest in a proteomic differential binding assay conducted using a protein microarray in accordance with the present invention. An aliquot of the complex sample originally run on the microarray is then run through the column. The protein of interest preferentially binds to the column and is thereby separated form other components of the sample. The bound protein is eluted and may then be used in further analyses 604, such as protein sequencing, tertiary structure determination, etc. In addition, data relating to the identification of the protein may be entered into bioinformatics databases for further research.

Alternatively, the same protein that bound the differentially expressed protein could be spotted repetitively on a chip and incubated with the an aliquot of the same lysate. The same protein should bind to the array, but in a much larger area than just the one spot on the original chip. Laser desorption mass spectrometry can then be used to sequence the protein directly from the chip, for example, by application of the SELDI technology by Ciphergen.

D. Vaccine Development

The arrays of the present invention may be usefully applied to the detection of antibodies in serum against potential protein antigens spotted on the array. This technique may be applied to vaccine development, as noted above and described below in Example 9. For example, sera from patients infected with a pathogen may be applied to an array of antigens to a particular pathogen expressed as GST-fusions (or other fusions), such as described with reference to FIG. 2F, above. These studies may help to determine immune response in these patients in order to identify immune-stimulating antigens. By discovering the appropriate antigens, new vaccines may be developed.

Antibody or other protein arrays can also be used to monitor the levels of a particular protein or groups of proteins (10,000–50,000, etc.). For example, the increase or decrease of a particular protein in a particular pathway can be monitored in response to treating a cell with a drug versus no treatment. Or protein levels can be monitored in animal or patient sera in response to an external stimulus such as a drug. Determining the impact of a putative drug treatment on a protein can aid in the discovery of a drug's mechanism of action.

E. Other Applications

The anticipated uses of proteomic microarray chips in accordance with the present invention are broad. Examples include monitoring the expression levels of specific proteins to decipher mechanisms of drug action or to discover new disease biomarkers, studying protein-protein interactions, or identifying potential antigens for vaccine development In general, the applications have in common the identification of a protein or set of proteins that are over-expressed or under-expressed in one complex mixture relative to another (or present/absent, such as in the case of a diagnostic protein). Those skilled in the art will recognize that embodiments of the present invention are compatible with a wide variety of assay formats including sandwich assay, such as ELISA.

As described above, protein microarrays may be used to determine differential expression of proteins in complex solutions by alternatively labeling (e.g., Cy 3 for one sample and Cy 5 for another) the two or more protein solutions to be compared. The chips may be used to find novel protein targets for later high throughput screening assays. In another particularly powerful application, the methodology may be used to purify a recombinant protein that is overexpressed in a particular host such as yeast or baculovirus. The sample that contains the expressed protein is compared to the sample that does not by co-binding the alternatively labeled samples on the chip, and looking for differentials. The procedure identifies proteins on the array that bind with reasonable affinity and specificity to the expressed protein. These same proteins are then used for generating chromatographic resins for the isolation and purification of the recombinant protein of interest.

In an analogous manner, the protein microarray chips may be used to find protein markers in plasma or serum that may be diagnostic of particular disease states such as cancer, HIV, or diabetes, or to find novel targets for drug screening. Also, once a set of protein-protein interactions has been identified for particular groups of proteins, it is possible to monitor the expression levels of these proteins to decipher mechanisms of drug action. In that regard, identified proteins may be used as probes of protein abundance, analogous to the ways in which antibodies are currently used to determine protein abundance. In addition, by examining the proteins from virulent and non-virulent strains of bacteria or viruses, one can determine unique virulence factors that result in infectious disease. Once these virulence factors are identified, these proteins can be used as targets for screening new anti-bacterial or anti-viral drugs.

In one embodiment, the protein microarrays of the invention are run in parallel with DNA arrays, and the differential binding results derived from each are compared to identify correlations in gene activity and protein expression. For example, differential binding assays are conducted for complex biological samples on both protein and DNA arrays. Separate aliquots from the samples are labeled and contacted with a protein microarray in accordance with the present invention and a DNA microarray, such as are well known in the art. The differential protein expression evidenced by the binding results on the protein array when compared with those for the DNA array may elucidate relationships between protein expression and gene families whose activation is required for that expression.

Another technique that may be combined with the proteomic microarray techniques of the present invention is the MS/MS macromolecular structural analysis technique described in U.S. patent application Ser. No. 09/580,380, incorporated by reference herein. In this way, the combination of techniques can be used to identify a protein of interest, enrich and isolate it, sequence the protein, and elucidate aspects of its tertiary protein structure.

Data relating to the identification and post-array processing of proteins of interest may also be entered into bioinfomatics databases. The data may be correlated with other biological data therein for further research.

4. Kits

Also provided by the subject invention are kits for performing proteomic binding assays using the subject arrays. Such kits according to the present invention will at least include an protein microarray according to the invention. The kits may be configured for analytical or diagnostic purposes, and may further include one or more additional reagents employed in the method for which the array is intended. For example, the kit may include various receptacles, labels, buffer solutions, tools and any other material necessary to conduct a proteomic binding assay. Kits in accordance with the present invention may also be configured to receive samples for analysis and thereafter perform the steps necessary for a binding assay in accordance with the invention without further user manipulation.

EXAMPLES

The following examples provide details concerning the synthesis and characteristics of the protein arrays in accordance with the present invention, their components, and applications. It should be understood the following is representative only, and that the invention is not limited by the detail set forth in these examples.

Example 1

Method Used to Make Silanized Slides

Slide preparation: Glass microscope slides were pre-cleaned by sonicating in a soap bath for 10 minutes, followed by high pressure de-ionized water wash. The slides were further cleaned 5 min in Nochromix/$H_2SO_4$, rinsed with high pressure de-ionized water wash. Finally, they were immersed for 5 minutes in isopropyl alcohol and dried with a stream of $N_2$. Pre-cleaned slides are also commercially available from, for example, Erie Scientific (Ultraclean) or Bioslide (Superclean).

E-beam: A CHA SEC-600-RAP e-beam was fitted with special wafer-sized inserts in the planetaries to accommodate the rectangular shape of the glass microscope slides. The e-beam crucibles were loaded with aluminum metal and fresh $SiO_2$. The chamber was then pumped down to at least $2\times10^{-7}$ torr. After pumpdown, the planetaries containing the slides were rotated (to allow even coating) while the high voltage (about 10 V) was applied. The electron beam vaporized the material in the crucible. First, 1000 Å of aluminum was deposited. After cooling, 800 Å of $SiO_2$ was evaporated. Film thickness during deposition was monitored by an oscillating gold-coated quartz crystal microbalance.

Vapor phase silanization: A vacuum oven was equilibrated to 100° C. 30–50 mL of fresh aminopropyltriethoxysilane (APS) was added to a wide (3–5") TEFLON evaporating dish. The slides were placed in the oven with the dish. The oven was then evacuated to −23 in. Hg for 45 minutes. The silane dish was then removed and the slides were baked for another 15 minutes at 100° C. Temperatures from about 50–150° C. and pressures from −10 to −50 in. Hg and baking times from 15 min. to 2 hours may also be used.

Example 2

Use of a Homobifunctional Adapter

Amine functionalized substrate surfaces were derivatized with an activated ester by reacting amine groups displayed on the substrate surface with the homobifunctional crosslinker bis-NHS ester. The NHS ester at one terminus of the adapter reacted with the amines on the substrate to produce an NHS ester functionalized slide as follows: 50 mg of adaptor was dissolved in 30 mL DMF, then 170 mL of 1×PBS or other suitable buffer was added. This was applied to the slides and incubated 1–2 hours with mixing. The slides were then rinsed in deionized water. The solution should be fresh to ensure that the NHS ester has not hydrolyzed.) Proteins containing exposed amine groups were spotted onto such a slide to produce covalently bound protein microarrays.

Example 3

Use of a Heterobifunctional Maleimide Adapter

Amine functionalized substrate surfaces were derivatized with maleimide groups by reacting amine groups displayed on the substrate surface with heterobifunctional crosslinkers. SMCC (having an N-hydroxysuccinimide (NHS) ester at one terminus, and a maleimide group at the other) was applied using the same protocol described above in Example 2. The NHS ester reacted with the amines on the substrate to produce a maleimide functionalized slide. Proteins containing exposed thiol groups were spotted onto such a slide to produce covalently bound protein microarrays.

Example 4

Use of a Heterobifunctional Biotin Adapter

Amine functionalized substrate surfaces were derivatized with biotin by reacting the amine groups with activated biotin molecules having an NHS ester at one terminus and a biotin group at the other. Aluminum/oxide slides coated with aminosilane were dipped into a solution of NHS-LC-LC-biotin ("LC" refers to 6-aminohexanoyl and "NHS" refers to N-hydroxysuccinimidyl) (commercially available from Pierce) that was 0.39 mM in PBS buffer. The slides were coated for 1.5 hours with shaking at 80 rpm. Such a surface can be used to attach, via robotic spotting, a variety of protein-avidin conjugates for displaying protein arrays.

Example 5

Use of a Heterobifunctional Biotin/Avidin Adapter

The Biotinylated slides described in Example 4 were be coated with a layer of avidin, streptavidin or any other avidin analog. After attachment of biotin, the slides were rinsed with water, then dipped in a solution of 1 µg/ml–1 mg/ml avidin, streptavidin or neutravidin in PBS buffer for 2 hours, stirring at 70 rpm. The slides were rinsed with water and ready for spotting biotinylated proteins. The various surface modification steps was followed using ellipsometry to note the thickness changes. A thickness change increase of 40–45 angstroms was reproducibly recorded after the addition of avidin to the surface layers. Because of the tetrameric nature of the avidin protein, sites are still available even after the avidin has bound to the biotinylated slide, therefore, biotinylated proteins may then be spotted on the avidin-treated slides. The reaction is facile and well within the lifetime of a 1 nL spotted droplet.

Example 6

Addition of Biotinylated Proteins to Biotin/Avidin Adapter

The avidin-treated slides of Example 5 were further derivatized by dip-coating into a solution of biotinylated Protein A or Protein G. In this manner, a Protein-A/G derivatized surface was generated. Chips functionalized with avidin were immersed in a solution of biotinylated Protein A or Protein G (Pierce product numbers 29989zz and 29988zz) (0.5–1 mg/mL in PBS buffer) for 2 hours at room temperature. The slides were then rinsed with de-ionized distilled water and blown dry with nitrogen or argon. The surfaces were then ready for spotting of antibodies.

Example 7

Protein Labeling

Protein solutions were adjusted to a concentration of 1 mg/mL in 0.1 M sodium carbonate, pH 9.3 and a volume of 0.1–1 mL, and mixed with bifunctional or mono-functional amine-reactive cyanine dye (Cy3 or Cy5, Amersham Pharmacia). The protein was purified from the unreacted dye by size exclusion chromatography using a Sephadex G-25 packing in a 5 cm long, 1.7 cm diameter column with a 1 mL load, 0.5 mL fractions, and a dilution factor of 3.5.

Example 8

Chip Binding Experiments

Protein microarrays in accordance with the present invention are chemically blocked with a polyethylene glycol (PEG) analog, modified at each terminus so that it will react with and bind to the amino-modified substrate surface not occupied by array elements. For example, the blocking agent may be a dithiol-modified PEG (SH-PEG-SH) applied with casein after the array element spotting is completed, as described above. A 30–100 µL aliquot of the probe solution is applied to the chip surface, and a clean coverslip placed on top, forming a sandwich of the probe solution on the chip surface. The protein solution is incubated with the chip for at least 1 hour. The coverslip is removed in 1×PBS/0.05% Tween or other suitable buffer containing surfactant. The chip is then washed in 1×PBS/0.05% Tween or other suitable buffer/surfactant system. The chips are further rinsed with water, dried under a stream of Argon or Nitrogen and scanned.

Example 9

Fusion Protein Arrays for Vaccine Development

*Chlamydia pneumoniae* (*C. pneumoniae*) is pathogen responsible for pneumonia and upper respiratory tract disease (e.g., bronchitis and sinusitis), and there is also a strong association between *C. pneumoniae* infection and heart disease and arteriosclerosis. In order to determine whether there is a different humoral response in patients developing one or the other (or both) type(s) of the pathology, an array of proteins expressed as GST-fusions, such as described with reference to FIG. 2F, above, was constructed using two hundred potential antigens predicted by in silico analysis to be surface exposed, secreted or specific to *C. pneumoniae*. Sera from fifty human patients infected with the pathogen and samples from patients with pneumonia, heart disease and arteriosclerosis will be applied to the array. The goal of these studies is to determine immune response in these patients in order to identify immune-stimulating antigens. Also, these studies will help elucidate the differences between immune response for patients presenting with heart disease versus patients presenting with pneumonia, etc. By discovering the appropriate antigens, new vaccines may be developed.

Example 10

Proof of Concept for Protein-GST Fusion Arrays

As proof of concept, a mouse serum raised against a recombinant *C. pneumoniae* protein-GST fusion was used as a control. GST fusions of known mouse antigens were spotted onto glutathione-treated substrates. Slides were blocked in casein. The mouse sera (known to contain antibodies to the spotted antigens) were diluted 100× in 1×TBS containing casein and 32 uL was deposited per slide, sandwiched under coverslip, and incubated overnight. Then, the arrays were washed with 1×TBS, 0.05% tween 20, and then de-ioized water. 32 uL of diluted anti-mouse antibody labelled with phycoerythrin was applied per slide. The slides were incubated for about 2 hours, washed as above and scanned. Strong signals were obtained from the mouse antigen spots as predicted based on the known composition of the sera containing antibodies.

Example 11

Proof of Concept "Spike" Experiment

As a proof of concept for the use of protein arrays in accordance with the present invention to resolve specific protein binding from complex mixtures, such as lysates and sera, "sample" and "control" lysates were prepared and run on sample protein arrays in accordance with the present invention. A "sample" was prepared by spiking unlabelled VEGF protein into an unlabelled lysate. The "control" was a non-VEGF spiked lysate. All proteins in the sample were labeled with Cy5 (red) and all proteins in the control were labeled with Cy3 (green). The two lysates were then mixed together and probed by application to a protein array in accordance with the present invention displaying a variety of spotted antibodies (FGF, VEGF, PSA, MMP9, MMP2) and conventional casein blocking on a maleimide functionalized surface.

Initially, the experiment failed as the sample was either too dilute to detect the spiked VEGF, or the sample was too concentrated and non-specific protein binding resulted in a slide giving very high background. Protein array chips were then prepared with a modified blocking agent, namely casein (protein block) with added dithiol-modified PEG (SH-PEG-SH) (chemical block). The sample and control lysates were again run on the modified arrays and the VEGF antigen differential was detectable in the mixture at a concentration were the conventionally blocked slide would read black due to non-specific protein binding.

The experiment was run on slides having a variety of silicon dioxide thicknesses on Al-coated glass slides. It was observed that slides coated with 800 to 900 angstroms of oxide (with 800 judged to be optimal), provided better signal strength than other thicknesses, in particular better than thicker oxide coatings of about 1300 angstroms.

Conclusion

Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

What is claimed is:

1. A microarray, comprising:
   a solid substrate having a substantially planar surface comprising an organic chemically-modified dielectric-coated reflective metal;
   a plurality of array elements comprising proteins stably attached to the substrate surface; and
   a di-thiol modified polyethylene glycol non-protein chemical blocking agent and a protein blocking agent bound to the substrate surface not occupied by protein-binding agent array elements bound to the substrate surface.

2. The microarray of claim 1, wherein the proteins are directly attached to the substrate surface.

3. The microarray of claim 1, wherein the proteins are indirectly attached to the substrate surface via a chemical adapter.

4. The microarray of claim 1, wherein the reflective metal is selected from the group consisting of aluminum, gold, chromium, titanium, and platinum.

5. The microarray of claim 1, wherein the reflective metal is aluminum.

6. The microarray of claim 1, wherein the dielectric comprises a metal oxide selected from the group consisting of silicon oxide, silicon dioxide and aluminum oxide.

7. The microarray of claim 1, wherein the dielectric is silicon dioxide about 800 angstroms thick.

8. The microarray of claim 1, wherein the organic chemical modification comprises a functionalized silane molecule.

9. The microarray of claim 8, wherein the functionalized silane molecule is an amino-modified silane molecule.

10. The microarray of claim 1, wherein the reflective metal is disposed on a non-metallic solid substrate.

11. The microarray of claim 10, wherein the non-metallic solid substrate is selected from the group consisting of glasses and plastics.

12. The microarray of claim 11, wherein the non-metallic solid substrate is a glass microscope slide.

13. The microarray of claim 1, wherein the protein blocking agent is selected from the group consisting of casein, non-fat milk and BSA.

14. The microarray of claim 13, wherein the reflective metal is aluminum disposed on a glass slide, the dielectric coating is about 800 angstrom thick silicon dioxide, and the organic chemical modification comprises a functionalized silane molecule.

15. The microarray of claim 2, wherein the proteins are directly bound to a functional group of the substrate surface.

16. The microarray of claim 15, wherein the organic chemically-modified surface displays an amine and the proteins have an exposed, activated carboxylic acid group.

17. The microarray of claim 3, wherein the adapter comprises a homobifunctional organic linker designed or selected to stably attach to the substrate surface on one terminus and stably attach to a functional group on the proteins on the other terminus.

18. The microarray of claim 17, wherein the adapter comprises a bis-NHS activated ester.

19. The microarray of claim 17, wherein the adapter comprises a modified NHS activated ester.

20. The microarray of claim 19, wherein the modification to the NHS activated ester is a protein-binding functional group at a non-substrate bound terminus of the adapter.

21. The microarray of claim 20, wherein the protein-binding functional group is selected from the group consisting of maleimide, biotin, avidin, or avidin analog.

22. The microarray of claim 21, wherein the protein-binding functional group is maleimide and attached proteins comprise an exposed, reduced thiol group.

23. The microarray of claim 21, wherein the protein-binding functional group is biotin and the proteins are avidin conjugated.

24. The microarray of claim 21, wherein the protein-binding functional group is avidin and the attached proteins are biotinylated.

25. The microarray of claim 21, wherein the protein-binding functional group is a protein designed or selected to attach stably to a functional group on the protein array elements.

26. The microarray of claim 25, wherein the protein-binding functional group is Protein A or Protein G and the attached proteins are antibodies.

27. The microarray of claim 26, wherein the protein-binding functional group is glutathione and the attached proteins are GST-protein fusions.

28. A kit for use in performing a proteomic binding assay, said kit including an array comprising;
   a solid substrate having a substantially planar surface comprising an organic chemically-modified dielectric-coated reflective metal;
   a plurality of array elements comprising proteins stably attached to the substrate surface; and
   a di-thiol modified polyethylene glycol non-protein chemical blocking agent and a protein blocking agent bound to the substrate surface not occupied by protein-binding agent array elements bound to the substrate surface; and binding assay reagents.

29. The kit of claim 28, wherein in the array the reflective metal is aluminum, the dielectric coating is $SiO_2$, and the organic chemical modification is aminosilane.

30. The kit of claim 29, wherein the aminosilane is functionalized with a maleimide.

31. The kit of claim 29, wherein the reflective metal is aluminum disposed on a glass slide and the dielectric coating is about 800 angstrom thick silicon dioxide.

32. The kit of claim 28, wherein the protein blocking agent is selected from the group consisting of casein, non-fat milk and BSA.

33. The kit of claim 32, wherein the chemical blocking agent is di-thiol modified polyethylene glycol and the protein blocking agent is casein.

34. The microarray of claim 14, wherein the protein blocking agent is casein.

* * * * *